(12) United States Patent
Kim et al.

(10) Patent No.: US 10,090,479 B2
(45) Date of Patent: Oct. 2, 2018

(54) STRETCHABLE/FOLDABLE OPTOELECTRONIC DEVICE, METHOD OF MANUFACTURING THE SAME, AND APPARATUS INCLUDING THE STRETCHABLE/FOLDABLE OPTOELECTRONIC DEVICE

(71) Applicant: Samsung Electronics Co., Ltd., Suwon-si, Gyeonggi-do (KR)

(72) Inventors: Taeho Kim, Suwon-si (KR); Sangwon Kim, Seoul (KR); Seongjun Park, Seoul (KR); Sangmin Lee, Seoul (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 174 days.

(21) Appl. No.: 14/845,518

(22) Filed: Sep. 4, 2015

(65) Prior Publication Data

US 2016/0233447 A1    Aug. 11, 2016

(30) Foreign Application Priority Data

Oct. 2, 2014 (KR) ......................... 10-2014-0133557

(51) Int. Cl.
*A61B 5/02* (2006.01)
*H01L 51/00* (2006.01)
(Continued)

(52) U.S. Cl.
CPC ...... *H01L 51/0097* (2013.01); *A61B 5/02427* (2013.01); *A61B 5/6826* (2013.01);
(Continued)

(58) Field of Classification Search
CPC ............. H01L 51/0097; H01L 51/0035; H01L 51/0094; H01L 51/502; H01L 51/5056;
(Continued)

(56) References Cited

U.S. PATENT DOCUMENTS 8,217,381 B2    7/2012    Rogers et al.
8,729,597 B2    5/2014    Kim et al.
(Continued)

FOREIGN PATENT DOCUMENTS

CN    101855729 A    10/2010
CN    102217081 A    10/2011
(Continued)

OTHER PUBLICATIONS

European Extended Search Report dated Mar. 9, 2016 issued in corresponding European Patent Application No. 15186740.5.
(Continued)

*Primary Examiner* — Lindsey G Wehrheim
(74) *Attorney, Agent, or Firm* — Harness, Dickey & Pierce, P.L.C.

(57) ABSTRACT

Provided are a stretchable and/or foldable optoelectronic device, a method of manufacturing the same, and an apparatus including the stretchable and/or foldable optoelectronic device. A stretchable and/or foldable optoelectronic device may include an optoelectronic device portion on a substrate. The substrate may include an elastomeric polymer and may be stretchable. The optoelectronic device portion may be configured to have a wavy structure to be stretchable. The optoelectronic device portion may include a graphene layer and a quantum dot (QD)-containing layer. The stretchable and/or foldable optoelectronic device may further include a capping layer that includes an elastomeric polymer and is on the optoelectronic device portion. The stretchable and/or foldable optoelectronic device may further include a plastic material layer that contacts at least one surface of the optoelectronic device portion.

37 Claims, 39 Drawing Sheets
(9 of 39 Drawing Sheet(s) Filed in Color)

(51) Int. Cl.
*H01L 51/50* (2006.01)
*H01L 51/52* (2006.01)
*A61B 5/024* (2006.01)
*A61B 5/00* (2006.01)
*H01L 27/32* (2006.01)

(52) U.S. Cl.
CPC ...... *H01L 27/3225* (2013.01); *H01L 51/0035* (2013.01); *H01L 51/0094* (2013.01); *H01L 51/502* (2013.01); *H01L 51/5056* (2013.01); *H01L 51/5072* (2013.01); *H01L 51/5088* (2013.01); *H01L 51/52* (2013.01); *H01L 51/5206* (2013.01); *H01L 51/5209* (2013.01); *H01L 51/5225* (2013.01); *H01L 51/5234* (2013.01); *H01L 51/5253* (2013.01); *H01L 51/0034* (2013.01); *H01L 51/0037* (2013.01); *H01L 2251/301* (2013.01); *H01L 2251/5338* (2013.01); *H01L 2251/558* (2013.01); *Y02E 10/549* (2013.01); *Y02P 70/521* (2015.11)

(58) Field of Classification Search
CPC . H01L 51/5072; H01L 51/5088; H01L 51/52; H01L 51/5206; H01L 51/5209; H01L 51/5225; H01L 51/5234; H01L 51/5253; H01L 51/0034; H01L 51/0037; H01L 2251/301; H01L 2251/5338; H01L 2251/558; A61B 5/02427; A61B 5/6826; Y02P 70/521; Y02E 10/549
See application file for complete search history.

(56) References Cited

U.S. PATENT DOCUMENTS

| | | |
|---|---|---|
| 2006/0286785 A1 | 12/2006 | Rogers et al. |
| 2010/0059863 A1 | 3/2010 | Rogers et al. |
| 2012/0068154 A1 | 3/2012 | Hwang et al. |
| 2012/0165759 A1 | 6/2012 | Rogers et al. |
| 2013/0100618 A1 | 4/2013 | Rogers et al. |
| 2014/0264269 A1 | 9/2014 | Choi et al. |
| 2015/0001462 A1 | 1/2015 | Rogers et al. |
| 2015/0243920 A1* | 8/2015 | Edman ............... H01L 51/5016 257/13 |

FOREIGN PATENT DOCUMENTS

| | | |
|---|---|---|
| CN | 103441221 A | 12/2013 |
| KR | 10-0734842 B1 | 7/2007 |
| KR | 10-2012-0140053 A | 12/2012 |
| KR | 10-1357045 B1 | 2/2014 |

OTHER PUBLICATIONS

Irina Hlimonenko et al., "Waveform Analysis of Peripheral Pulse Wave Detected in the Fingertip with Photoplethysmograph", Measurement Science Review, vol. 3, Section 2, p. 49-52, 2003.
Chinese Office Action dated Jul. 26, 2017 issued in corresponding Chinese Application No. 201510647147.4 (English translation provided).

* cited by examiner

←→ stretching

←→ stretching

FIG. 30A
FIG. 30B
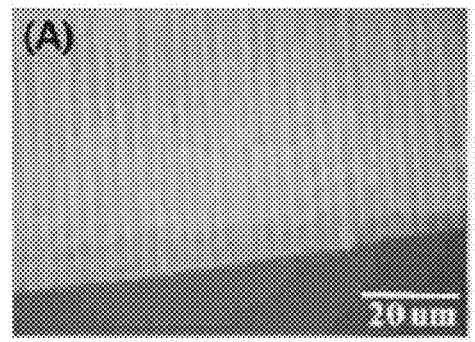
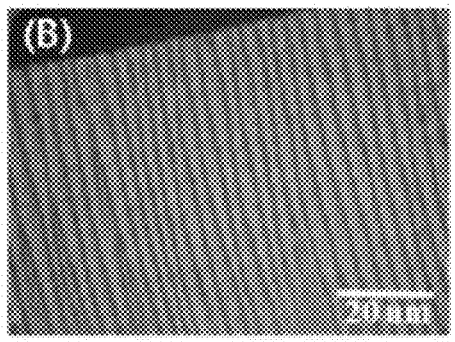
FIG. 30C
FIG. 30D
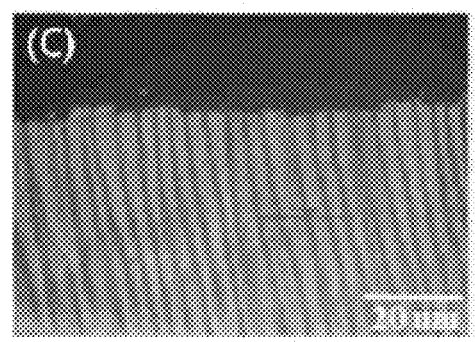
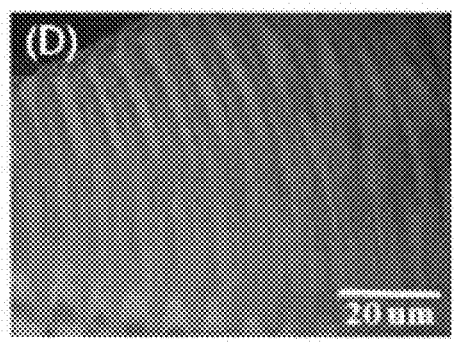
FIG. 31
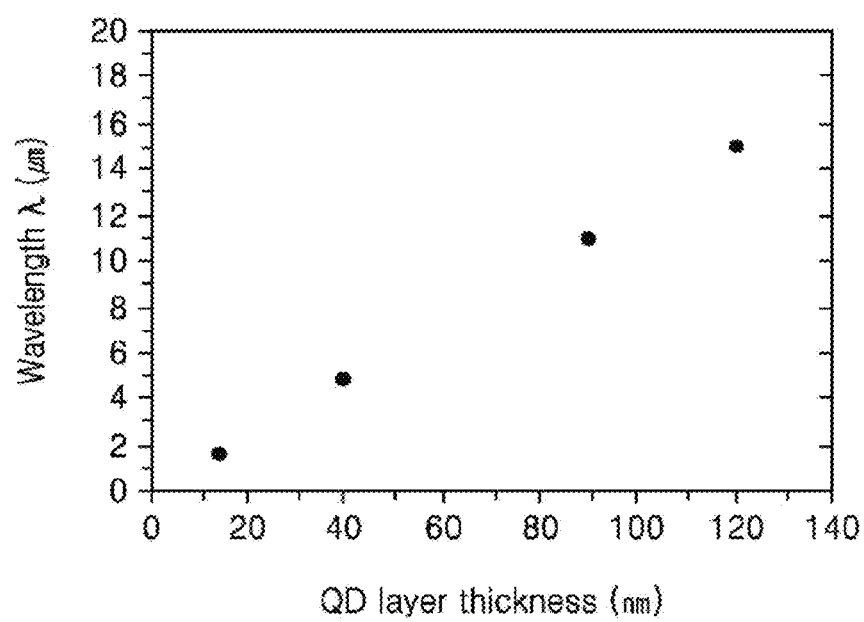

(A) Uniaxial wavy (B) Multiaxial wavy

FIG. 34A
FIG. 34B
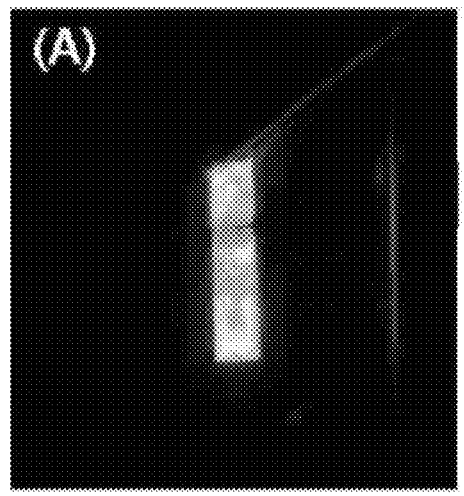
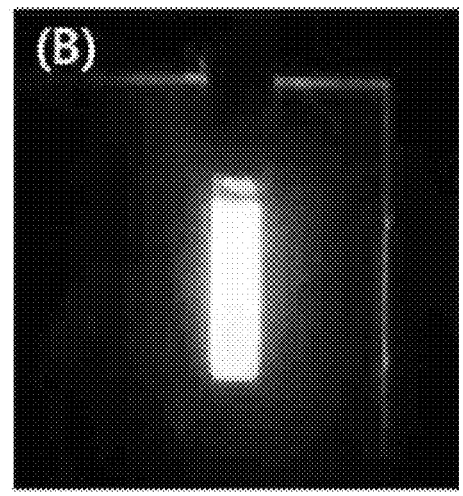
FIG. 35
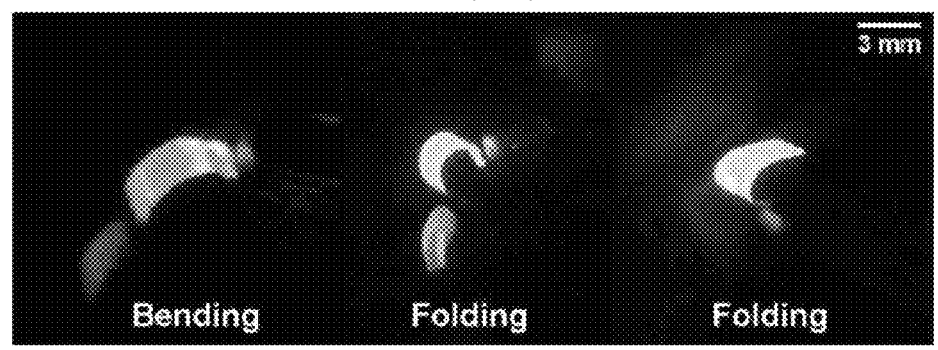

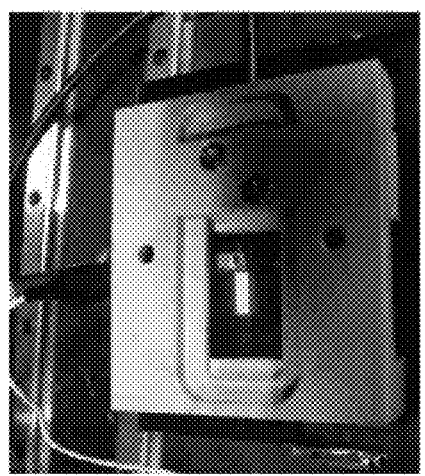
FIG. 44
FIG. 45C  8%  stretching
FIG. 45B  3%  stretching
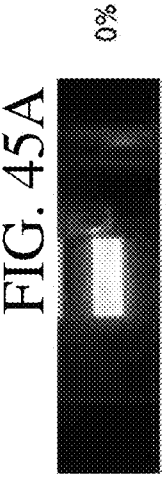
FIG. 45A  0%  stretching

STRETCHABLE/FOLDABLE OPTOELECTRONIC DEVICE, METHOD OF MANUFACTURING THE SAME, AND APPARATUS INCLUDING THE STRETCHABLE/FOLDABLE OPTOELECTRONIC DEVICE

RELATED APPLICATION

This application claims priority under 35 U.S.C. § 119 to Korean Patent Application No. 10-2014-0133557, filed on Oct. 2, 2014, in the Korean Intellectual Property Office, the entire disclosure of which is incorporated herein in its entirety by reference.

BACKGROUND

1. Field

The present disclosure relates to stretchable and/or foldable optoelectronic devices, methods of manufacturing the same, and/or apparatuses including the stretchable and/or foldable optoelectronic devices.

2. Description of Related Art

Recently, the interest in a flexible electronic apparatus has increased. Flexible electronics are a technology where an electronic circuit/apparatus may be bent or folded by mounting an electronic device on a bendable substrate such as a plastic substrate. In particular, flexible electronics have drawn attention as a next-generation technology in the field of displays.

The desire for a stretchable (extensible) electronic apparatus along with a flexible electronic apparatus has emerged. A flexible electronic apparatus may be bent while maintaining its length. A stretchable electronic apparatus may be bent and its length may also be increased. Thus, stretchable electronics are expected to be useful as a technology in new applications.

SUMMARY

The present disclosure relates to stretchable/foldable optoelectronic devices having excellent characteristics.

Provided are stretchable/foldable optoelectronic devices including a graphene and/or quantum dot (QD)-containing layer.

Provided are stretchable/foldable optoelectronic devices having excellent durability. Provided are stretchable/foldable optoelectronic devices that may normally operate without deteriorating characteristics and decreasing efficiency even through repeated stretching and/or folding operations.

Provided are stretchable/foldable optoelectronic devices having an active surface (e.g., a light-emitting surface) that is stretchable or foldable.

Provided are methods of manufacturing the stretchable/foldable optoelectronic devices.

Provided are apparatuses including the stretchable/foldable optoelectronic devices.

Additional aspects will be set forth in part in the description which follows and, in part, will be apparent from the description, or may be learned by practice of example embodiments.

According to example embodiments, a stretchable optoelectronic device includes: a substrate that includes an elastomeric polymer and is stretchable; and an optoelectronic device portion on the substrate. The optoelectronic device portion includes a graphene layer and a quantum dot (QD)-containing layer. The optoelectronic device portion is configured to have a wavy structure to be stretchable.

In example embodiments, the stretchable optoelectronic device may further include a capping layer that includes an elastomeric polymer. The capping layer may be stretchable. The capping layer may be on the optoelectronic device portion.

In example embodiments, the optoelectronic device portion may be located on a mechanical neutral plane (MNP), or around a MNP.

In example embodiments, the elastomeric polymer of the capping layer may include at least one of silicon-based polymer, polyurethane (PU), polyurethane acrylate (PUA), acrylate polymer, and acrylate terpolymer. The silicon-based polymer may include at least one of polydimethylsiloxane (PDMS), polyphenyl-methylsiloxane, and hexamethyldisiloxane.

In example embodiments, the stretchable optoelectronic device may further include a plastic material layer connected to a surface of the optoelectronic device portion. The plastic material layer may be between the substrate and the optoelectronic device portion or the optoelectronic device portion may be between the substrate and the plastic material layer.

In example embodiments, the plastic material layer may include at least one of polyethylene naphthalate (PEN), polyimide (PI), and polyethylene terephthalate (PET).

In example embodiments, the plastic material layer may have a thickness that ranges from about 0.5 μm to about 30 μm.

In example embodiments, the wavy structure of the optoelectronic device portion may have an average wavelength that ranges from about 10 μm to about 2 mm, and the wavy structure of the optoelectronic device portion may have an average amplitude that ranges from about 100 nm to about 1 mm.

In example embodiments, the optoelectronic device portion may be one of a light-emitting device portion, a photovoltaic device portion, and a photo-detecting device portion.

In example embodiments, the optoelectronic device portion may include a first electrode on the substrate, a light-emitting layer on the first electrode, and a second electrode on the light-emitting layer. One of the first and second electrodes may be an anode. The anode may include the graphene layer, and the light-emitting layer includes the QD-containing layer.

In example embodiments, the optoelectronic device portion may further include at least one of: a hole transport layer (HTL) between the anode and the light-emitting layer; and an electron transport layer (ETL) between the light-emitting layer and a cathode from among the first and second electrodes.

In example embodiments, the optoelectronic device portion may further include a hole injection layer (HIL) between the anode and the HTL.

In example embodiments, the optoelectronic device portion may further include a poly(3,4-ethylenedioxythiophene) (PEDOT) layer that contacts the graphene layer.

In example embodiments, the graphene layer may be doped with a p-type dopant.

In example embodiments, the elastomeric polymer of the substrate may include at least one of silicon-based polymer, polyurethane (PU), polyurethane acrylate (PUA), acrylate polymer, and acrylate terpolymer. The silicon-based polymer may include at least one of polydimethylsiloxane (PDMS), polyphenyl-methylsiloxane, and hexamethyldisiloxane.

In example embodiments, the stretchable optoelectronic device may have strain that is equal to or greater than 5%.

In example embodiments, the stretchable optoelectronic device may be a foldable device.

According to example embodiments, an apparatus may include the stretchable optoelectronic device and a circuit connected to the stretchable optoelectronic device.

According to example embodiments, a light-emitting device includes: a first material layer that includes an elastomeric polymer; a second material layer that faces the first material layer and includes an elastomeric polymer; and a light-emitting device portion that is between the first and second material layers. The light-emitting device portion includes a light-emitting layer including a quantum dot (QDs)-containing layer. The light-emitting device portion is configured so that a light-emitting surface of the light-emitting layer is one of stretchable and foldable.

In example embodiments, the light-emitting device portion may further include a graphene layer. The graphene layer may be between the light-emitting layer and one of the first material layer and the second material layer.

In example embodiments, the light-emitting device may further include a plastic layer that is between the light-emitting device portion and the one of the first material layer and the second material layer. The graphene layer may be between the plastic layer and the QD-containing layer.

In example embodiments, the plastic layer may include at least one of polyethylene naphthalate (PEN), polyimide (PI), and polyethylene terephthalate (PET).

The light-emitting device portion may include a first electrode, a hole transport layer (HTL), the light-emitting layer, an electron transport layer (ETL), and a second electrode that are sequentially stacked on the first material layer or the second material layer. The first electrode may include graphene.

In example embodiments, the light-emitting device portion may be configured to have a wavy structure In example embodiments, the elastomeric polymer in at least one of the first material layer and the second material layer may include at least one of silicon-based polymer, polyurethane (PU), polyurethane acrylate (PUA), acrylate polymer, and acrylate terpolymer.

In example embodiments, the silicon-based polymer may include at least one of polydimethylsiloxane (PDMS), polyphenylm-ethylsiloxane, and hexamethyldisiloxane.

According to example embodiments, an apparatus may include the light-emitting device and a circuit connected to the light-emitting device.

According to example embodiments, a method of manufacturing a stretchable optoelectronic device includes: forming a plastic layer on a first substrate; forming an optoelectronic device portion on the plastic layer, the optoelectronic device portion including a graphene layer and a quantum dot (QD)-containing layer; separating a stack structure from the first substrate, the stack structure including the plastic layer and the optoelectronic device portion; attaching the stack structure to the second substrate when the second substrate is horizontally stretched; and forming a wavy structure in the optoelectronic device portion by removing a tensile strain applied to the second substrate.

In example embodiments, the method may further include forming a capping layer including an elastomeric polymer on the optoelectronic device portion.

In example embodiments, the elastomeric polymer of the capping layer may include at least one of polyurethane (PU), polyurethane acrylate (PUA), acrylate polymer, acrylate terpolymer, and silicon-based polymer. The silicon-based polymer may include at least one of PDMS, polyphenyl-methylsiloxane, and hexamethyldisiloxane.

In example embodiments, plastic layer may include at least one of polyethylene naphthalate (PEN), polyimide (PI), and polyethylene terephthalate (PET).

In example embodiments, the forming optoelectronic device portion on the plastic layer may include sequentially forming a first electrode, a hole transport layer (HTL), a light-emitting layer, an electron transport layer (ETL), and a second electrode on the plastic layer. The first electrode may include the graphene layer. The light-emitting layer may include the QD-containing layer.

In example embodiments, the attaching the stack structure to the second substrate may include disposing the plastic layer between the second substrate and the optoelectronic device portion.

In example embodiments, the attaching the stack structure to the second substrate may include disposing the optoelectronic device portion between the second substrate and the plastic layer.

In example embodiments, the attaching the stack structure to the second substrate may include disposing an adhesive layer between the second substrate and the optoelectronic device portion.

In example embodiments, the elastomeric polymer of the second substrate may include at least one of silicon-based polymer, polyurethane (PU), polyurethane acrylate (PUA), acrylate polymer, and acrylate terpolymer. The silicon-based polymer may include at least one of polydimethylsiloxane (PDMS), polyphenylm-ethylsiloxane, and hexamethyldisiloxane. In example embodiments, the first substrate may include a polymer substrate on a rigid substrate. The rigid substrate may be more rigid than the polymer substrate. The rigid substrate may be a glass substrate.

According to example embodiments, a method of manufacturing a stretchable optoelectronic device includes: horizontally stretching a substrate including an elastomeric polymer to transform the substrate to a stretched substrate; forming an optoelectronic device portion including a graphene layer and a quantum dot (QD)-containing layer on the stretched substrate; and forming a wavy structure in the optoelectronic device portion by removing a tensile strain applied to the substrate.

In example embodiments, the graphene layer may contact the substrate when the forming the optoelectronic device portion.

In example embodiments, the forming the optoelectronic device portion on the stretched substrate may include sequentially forming a first electrode, a hole transport layer (HTL), a light-emitting layer, an electron transport layer (ETL), and a second electrode on the stretched substrate. The first electrode may include the graphene layer and the light-emitting layer may include the QD-containing layer.

In example embodiments, the forming the optoelectronic device portion may include forming the optoelectronic device portion on an other substrate and then attaching the optoelectronic device portion to the stretched substrate. The QD-containing layer may be between the stretched substrate and the graphene layer.

In example embodiments, the method may further include forming a capping layer including an elastomeric polymer on the optoelectronic device portion.

In example embodiments, the elastomeric polymer of the substrate may include at least one of silicon-based polymer, polyurethane (PU), polyurethane acrylate (PUA), acrylate polymer, and acrylate terpolymer. The silicon-based polymer may include at least one selected of polydimethylsiloxane (PDMS), the group consisting of, and hexamethyldisiloxane.

According to example embodiments, a stretchable optoelectronic device includes a substrate and an optoelectronic device portion on the substrate. The substrate includes an elastomeric polymer that is stretchable. The optoelectronic device portion includes a graphene layer and an active layer. The active layer is on the graphene layer or between the graphene layer and the substrate. The active layer includes one of quantum dots, light-emitting nanomaterials, and a transition metal dichalocogenide (TMDC) layer. The optoelectronic device portion is configured to have a wavy structure if the substrate is not subject to a tensile stress. The optoelectronic device is configured to transition from the wavy structure to a planar structure based on a level of the tensile stress applied to the substrate.

In example embodiments, the elastomeric polymer of the substrate may include at least one of silicon-based polymer, polyurethane (PU), polyurethane acrylate (PUA), acrylate polymer, and acrylate terpolymer.

In example embodiments, the stretchable optoelectronic device may further include a capping layer on the optoelectronic device portion. The optoelectronic device portion may be between the first and second substrates. The capping layer may include at least one of silicon-based polymer, polyurethane (PU), polyurethane acrylate (PUA), acrylate polymer, and acrylate terpolymer.

In example embodiments, the active layer may include the quantum dots. The quantum dots may have one of a single-layer structure and a multi-layer structure.

In example embodiments, the graphene layer may be a first electrode of the optoelectronic device portion. The optoelectronic device portion may include a second electrode connected to the active layer. The optoelectronic device portion may include at least one of a hole transfer layer between the graphene layer and the active layer, and an electron transfer layer between the second electrode and the active layer.

In example embodiments, the active layer may directly contact at least one of the hole transfer layer and the electron transfer layer.

In example embodiments, the stretchable optoelectronic device may include a plastic material layer. The plastic material layer may include at least one of polyethylene naphthalate (PEN), polyimide (PI), and polyethylene terephthalate (PET). The plastic material layer may be one of on the optoelectronic device portion and between the optoelectronic device portion and the substrate.

In example embodiments, a sensor system may include a sensor system, including an electronic patch and a mobile equipment device. The electronic patch may include one of the above stretchable optoelectronic devices connected to a communication chip and an antenna. The mobile equipment device may be configured to exchange data and power signals with the electronic patch.

In example embodiments, the communication chip and the antenna in the electronic patch may be a first communication chip and a first antenna respectively. The mobile equipment device may include an application processor, a drive integrated circuit, and a second communication chip connected a second antenna.

In example embodiments, a sensor circuit may include a sensing unit, a filter circuit connected to the sensing unit, and a gain amplification circuit connected to the filter circuit.

In example embodiments, the filter circuit may include a high pass filter circuit connected to a low pass filter circuit. The high pass filter circuit may include two capacitors connected in series to a terminal of a first operational amplifier. The low pass filter circuit may include two resistors connected in series between an output terminal of the first operational amplifier and an input terminal of the second operational amplifier.

In example embodiments, the gain amplification circuit may include a gain operational amplifier connected to an output terminal of the second operational amplifier.

According to example embodiments, a method of manufacturing an stretchable optoelectronic device includes: forming or attaching an optoelectronic device portion on a substrate that is stretched; and forming a wavy structure in the optoelectronic device portion by removing a tensile strain applied to the substrate. The optoelectronic device portion includes a graphene layer and an active layer. The active layer is on the graphene layer or between the graphene layer and the substrate. The active layer includes one of quantum dots, light-emitting nanomaterials, and a transition metal dichalocogenide (TMDC) layer. The optoelectronic device portion is configured to transition from the wavy structure to a planar structure based on a level of the tensile stress applied to the substrate.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

The foregoing and other features of inventive concepts will be apparent from the more particular description of non-limiting embodiments of inventive concepts, as illustrated in the accompanying drawings in which like reference characters refer to like parts throughout the different views. The drawings are not necessarily to scale, emphasis instead being placed upon illustrating principles of inventive concepts. In the drawings:

Figure 1:
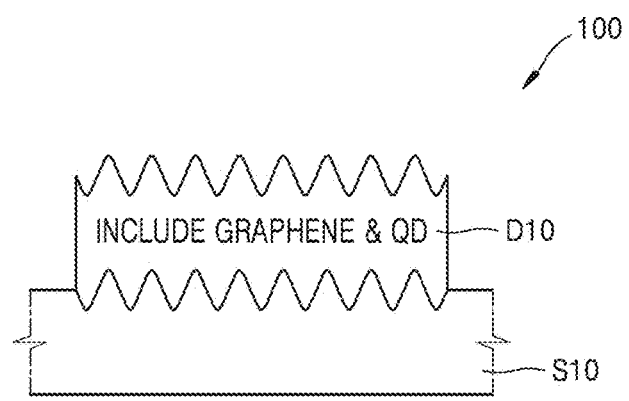
Figure 2:
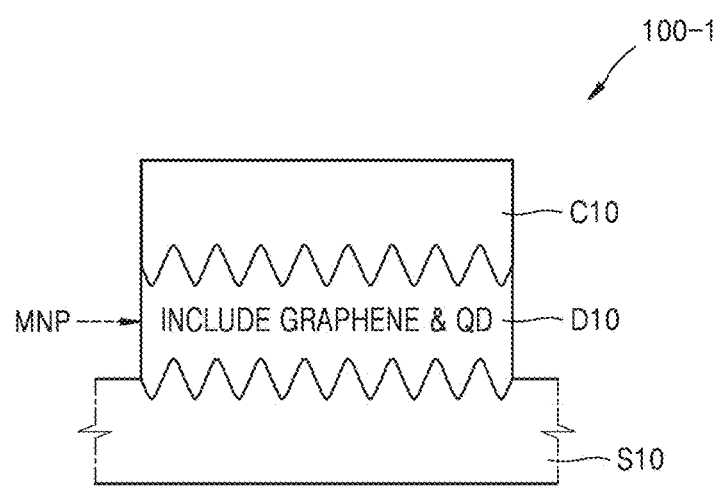
Figure 3:
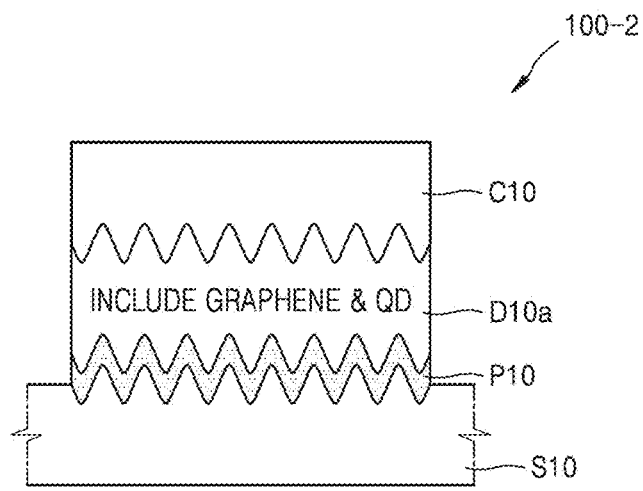
Figure 4:
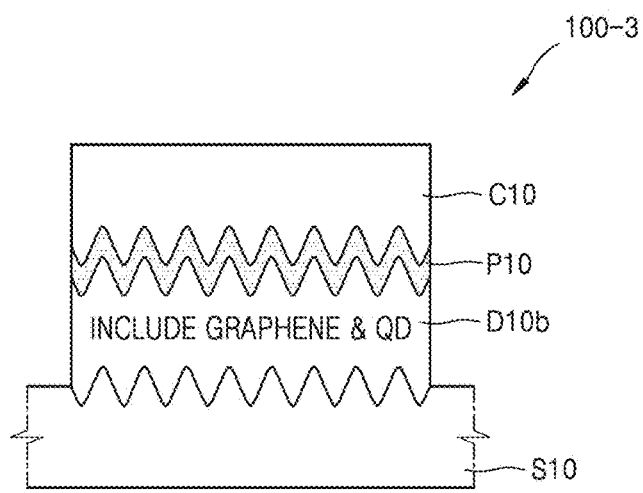
Figure 5:
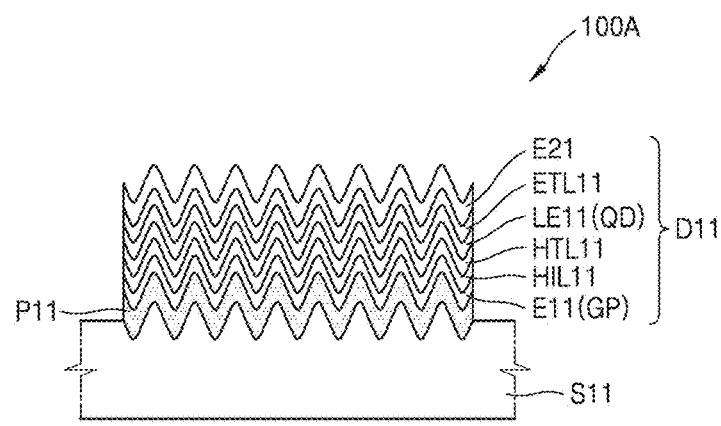
Figure 6:
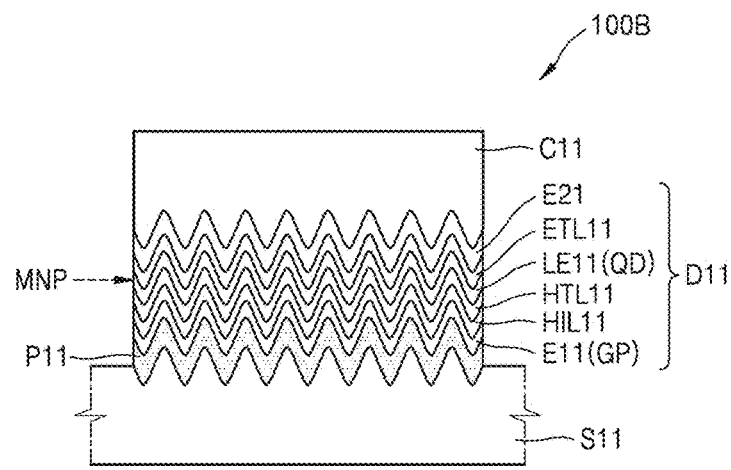
Figure 7:
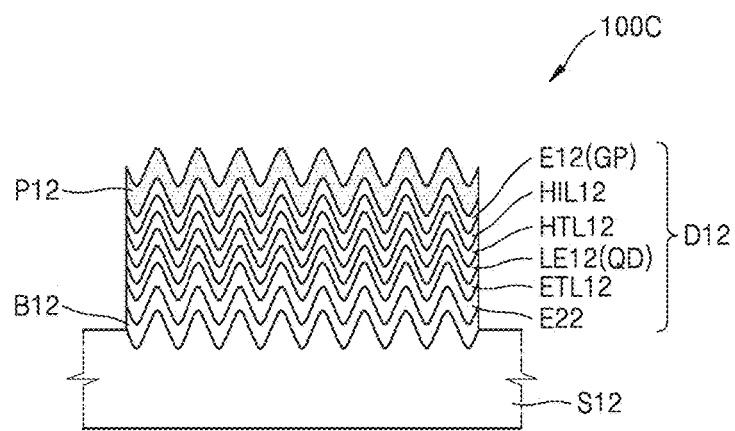
Figure 8:
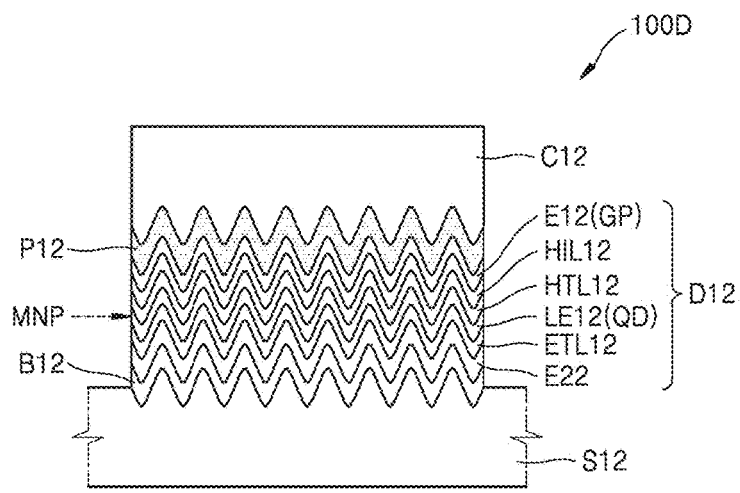
Figure 9:
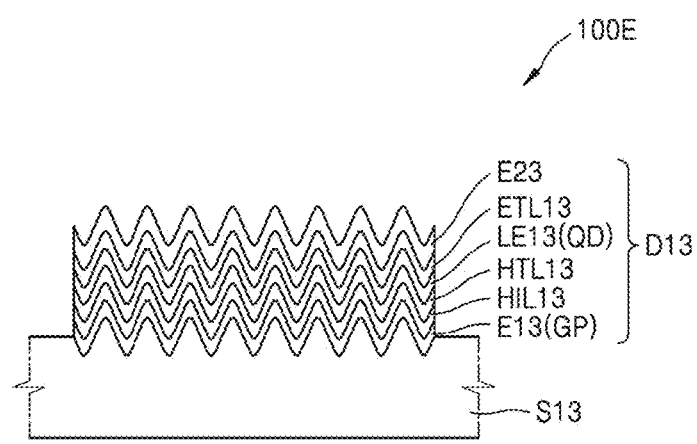
Figure 10:
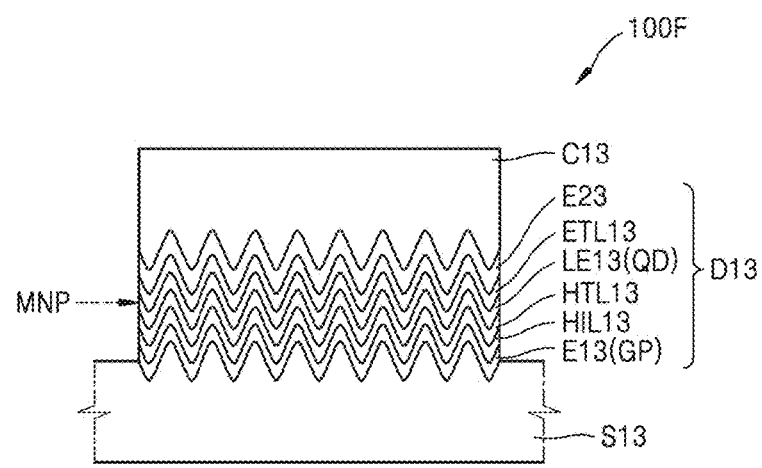
Figure 11:
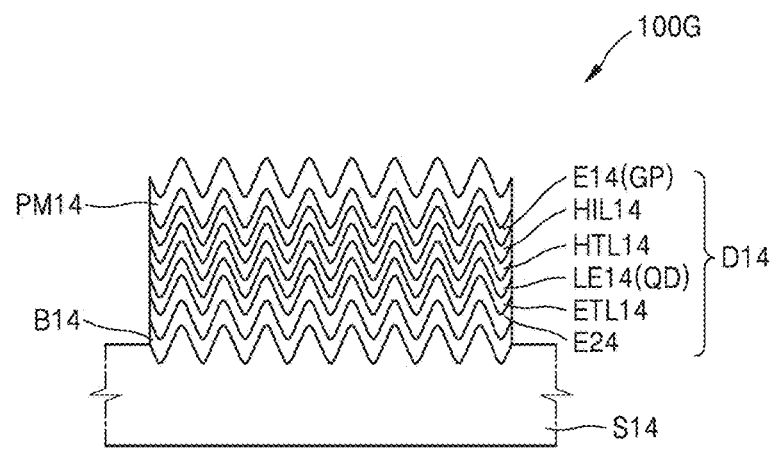
Figure 12:
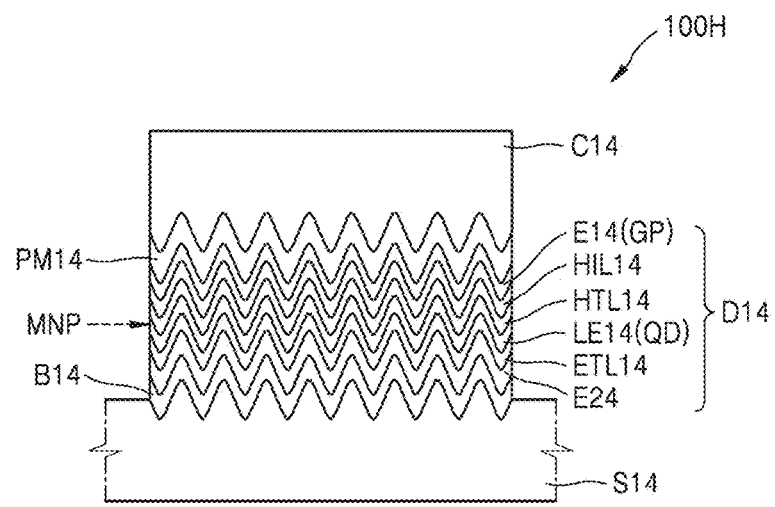
Figure 13:
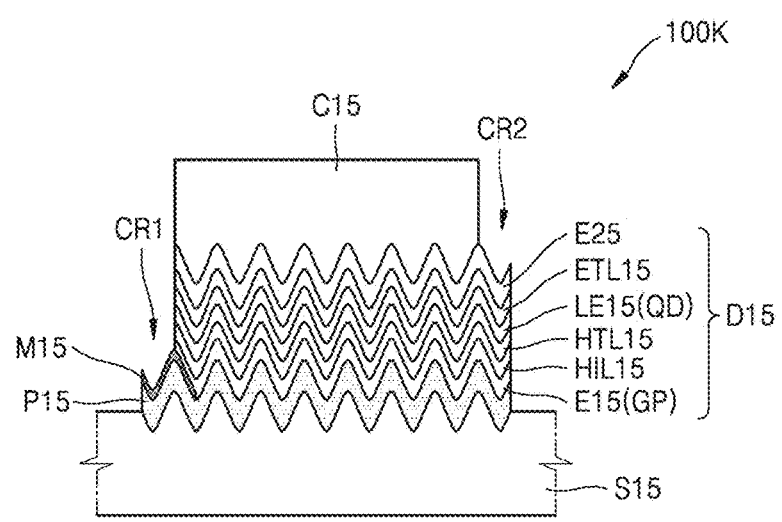
Figure 14:
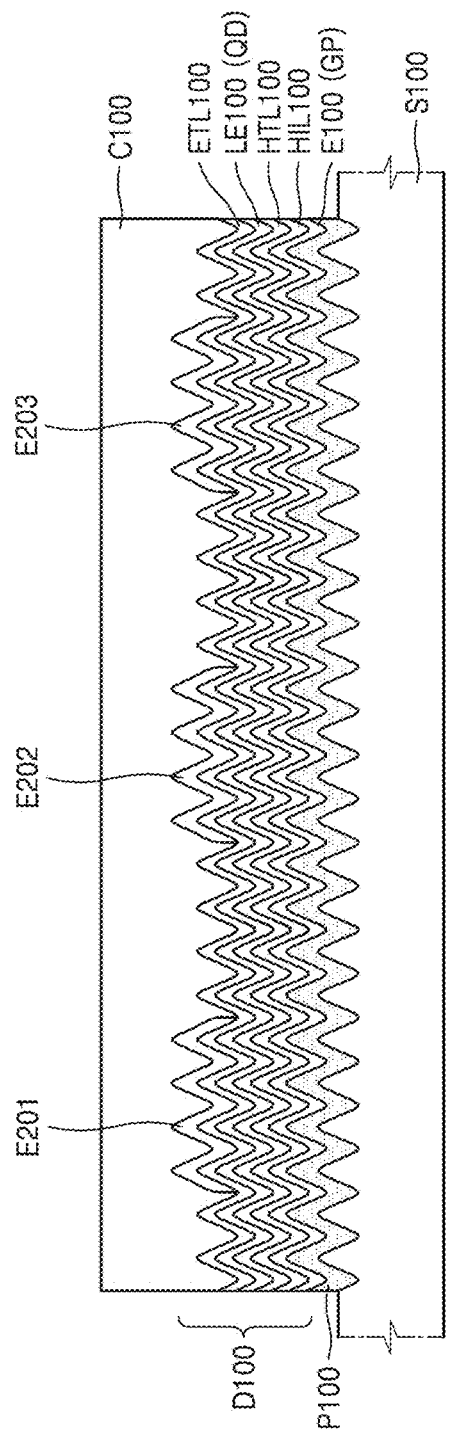
Figure 15:
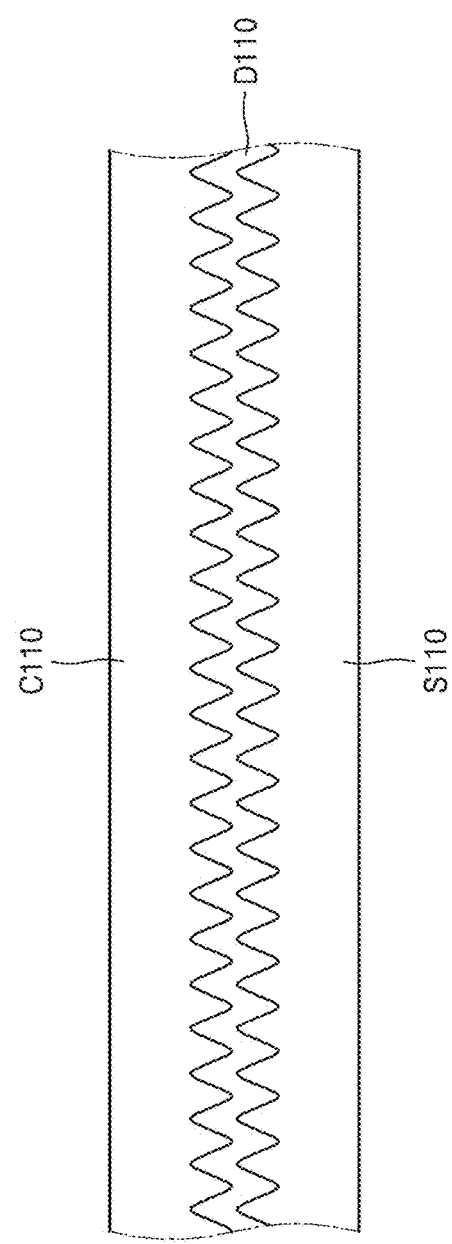
Figure 16:
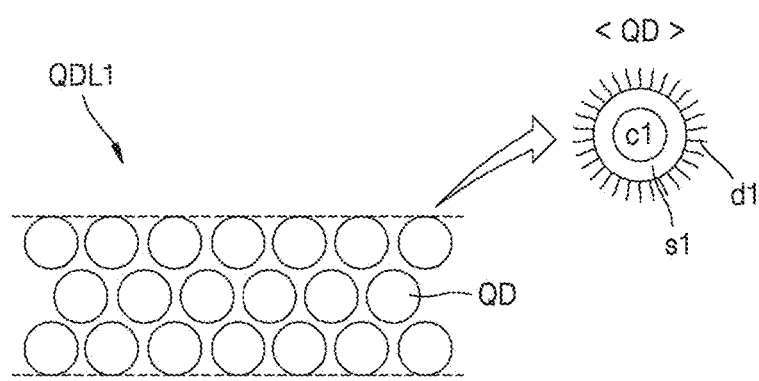
Figure 18:
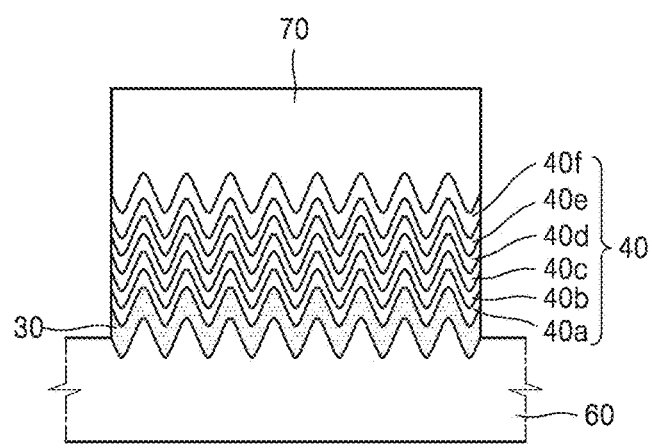
Figure 20:
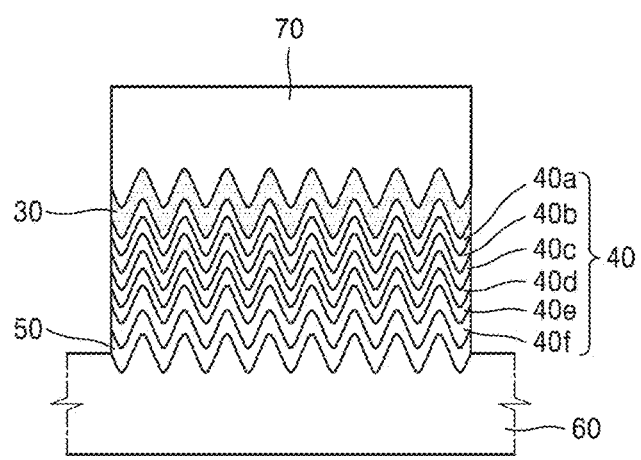
Figure 21A:
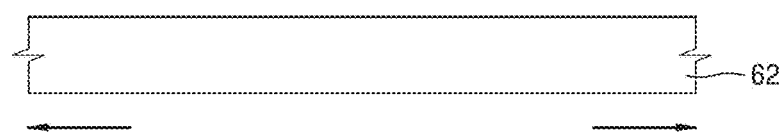
Figure 21B:
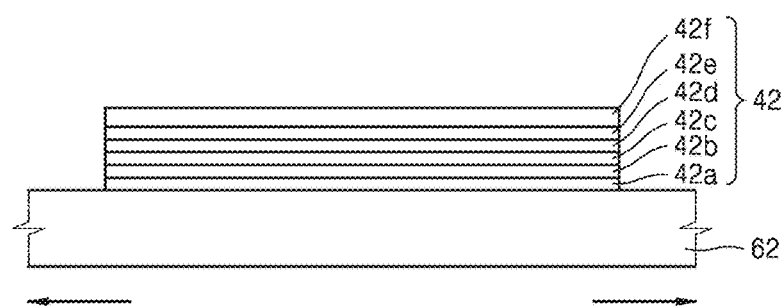
Figure 21C:
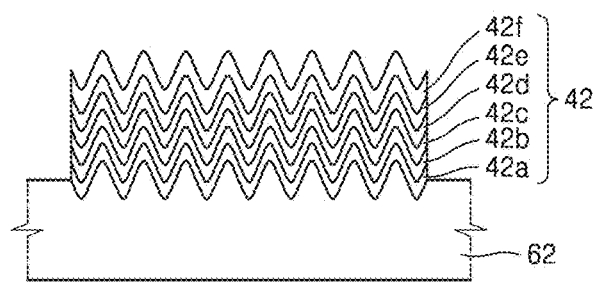
Figure 22:
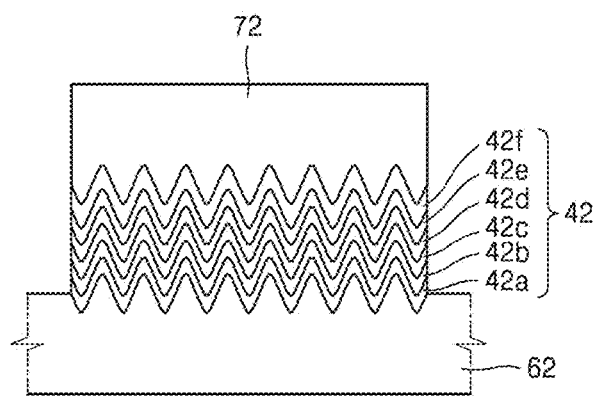
Figure 24:
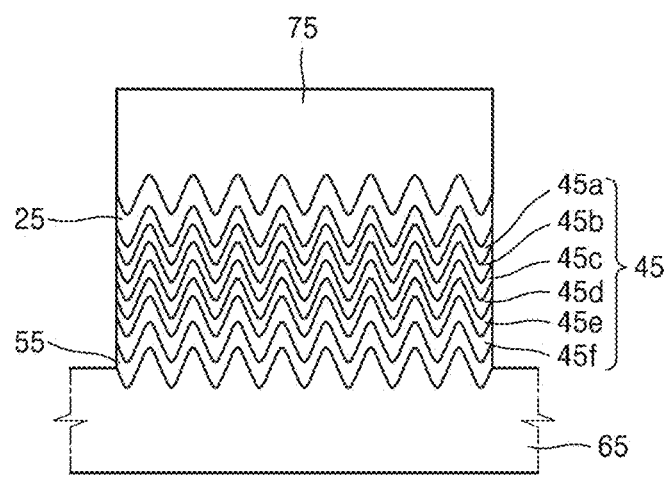
Figure 25:
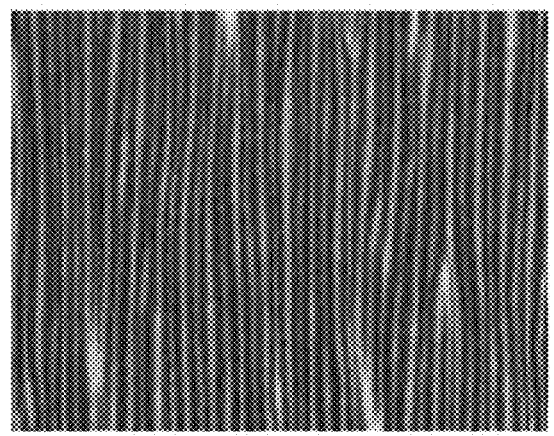
Figure 26:
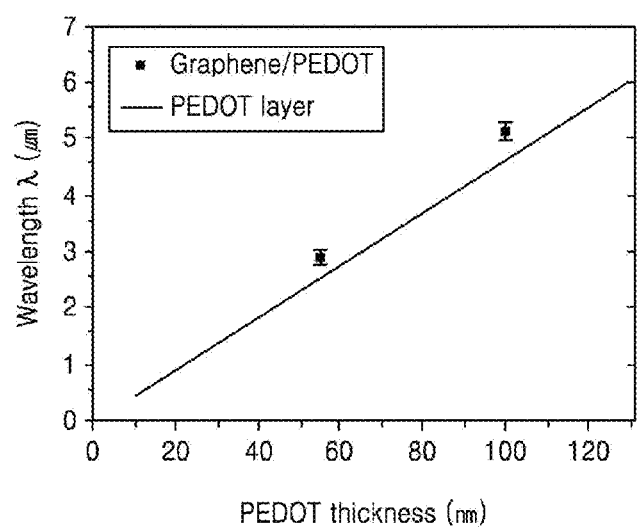
Figure 28:
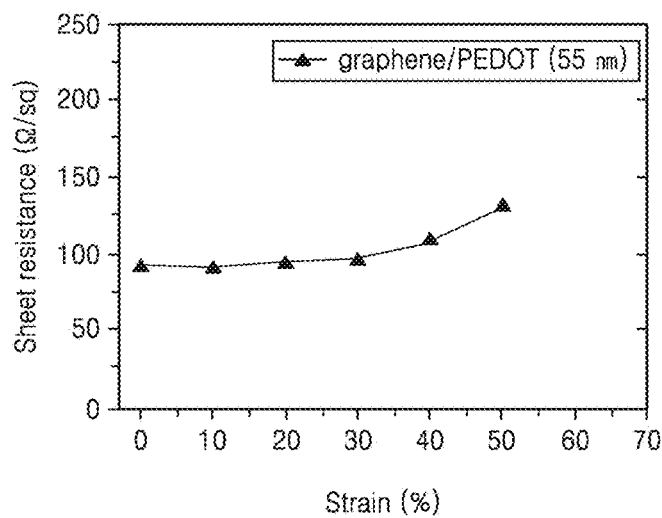
Figure 29:
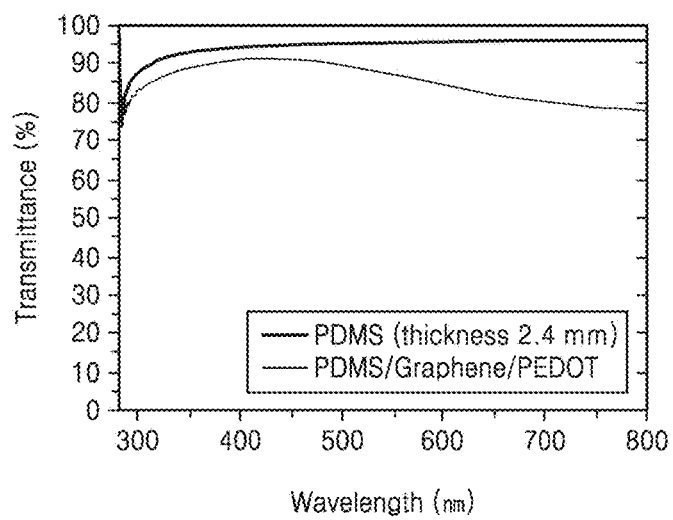
Figure 33A:
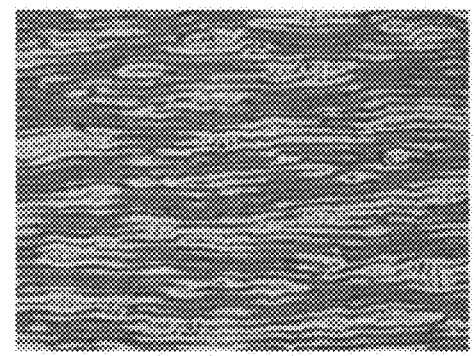
Figure 33B:
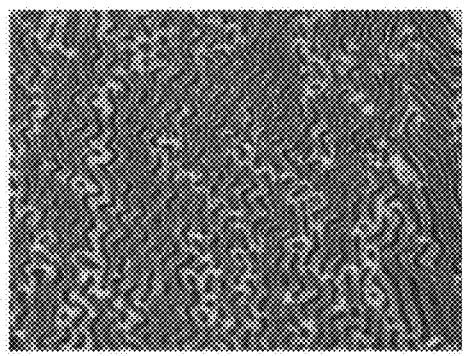
Figure 36C:
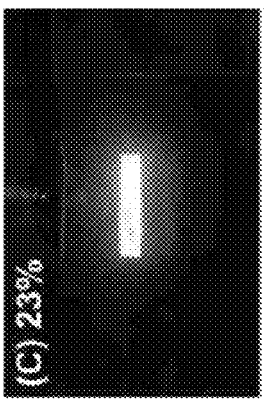
Figure 36B:
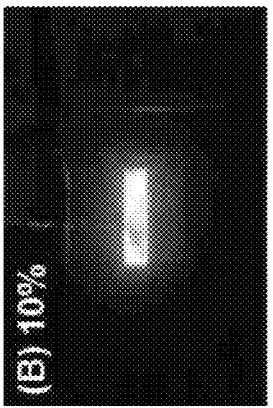
Figure 36A:
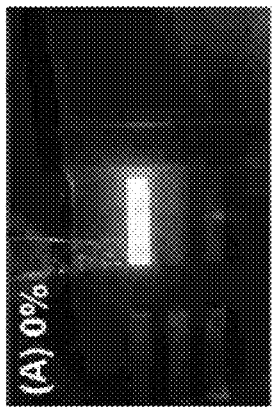
Figure 37:
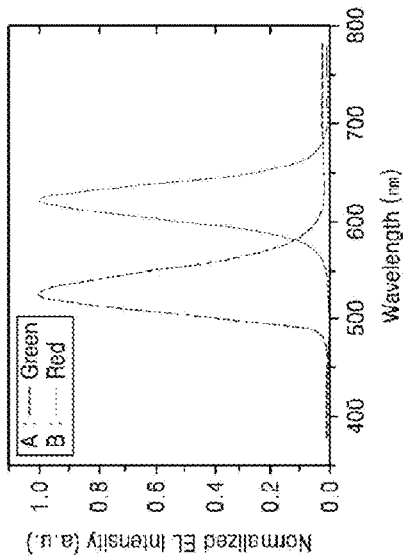
Figure 38:
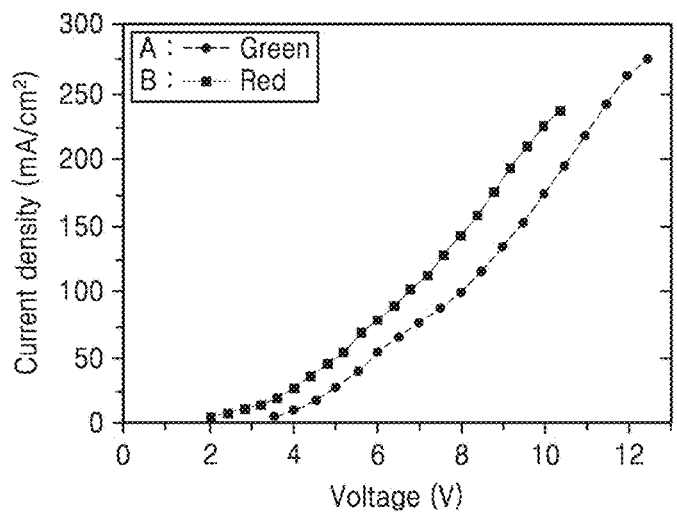
Figure 39:
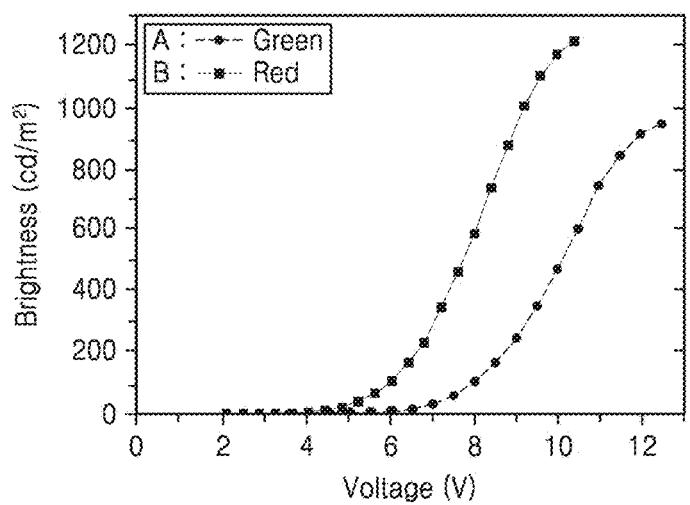
Figure 40:
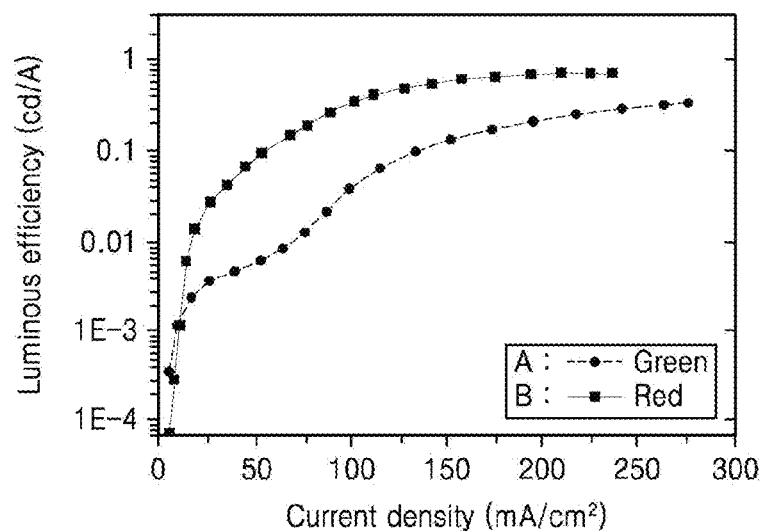
Figure 41:
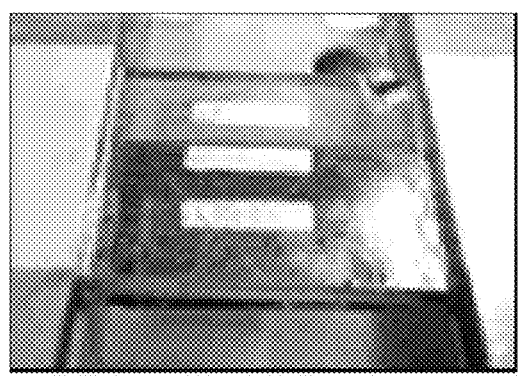
Figure 42:
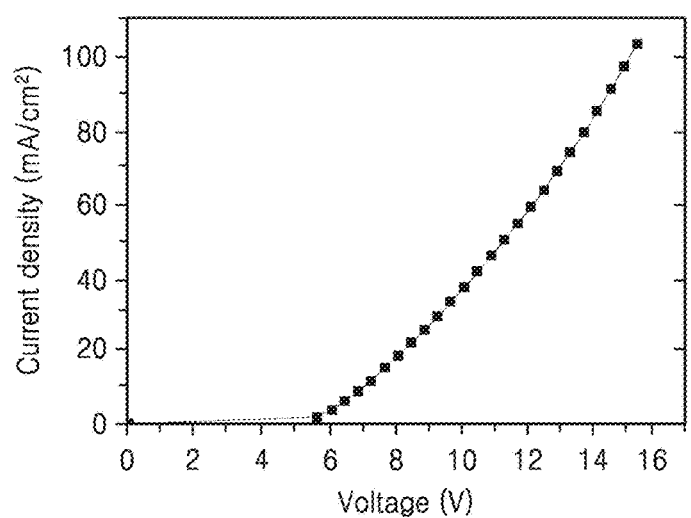
Figure 43:
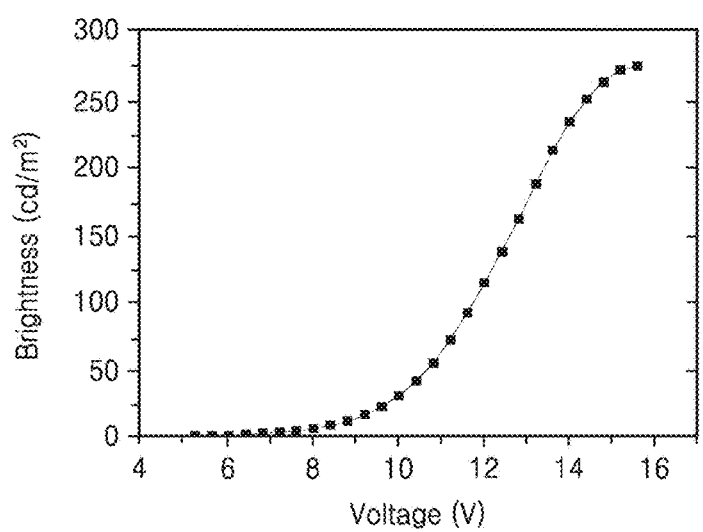
Figure 46:
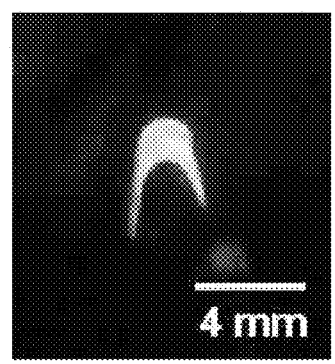
Figure 47:
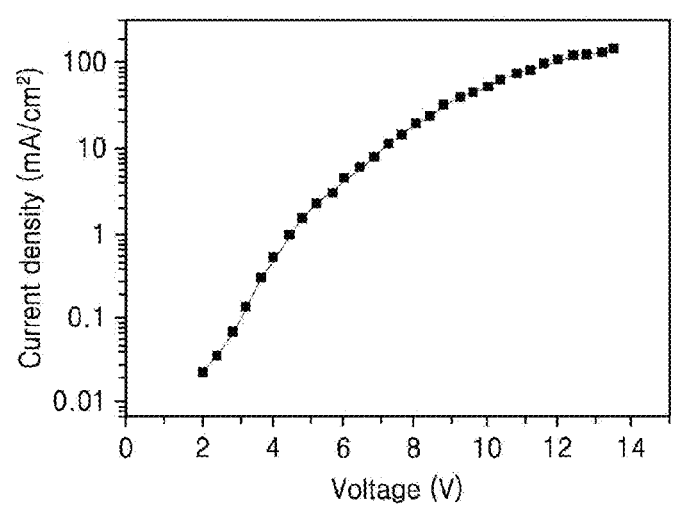
Figure 48:
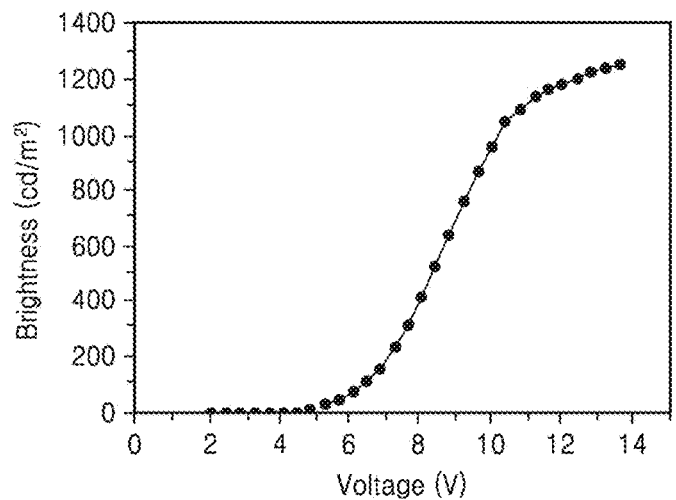
Figure 49:
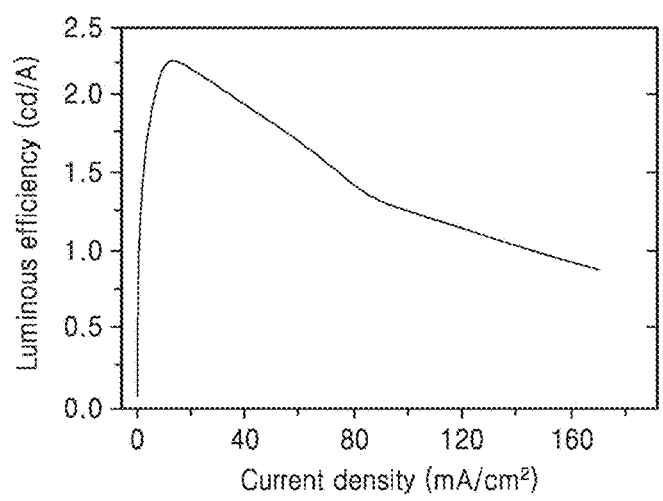
Figure 50:
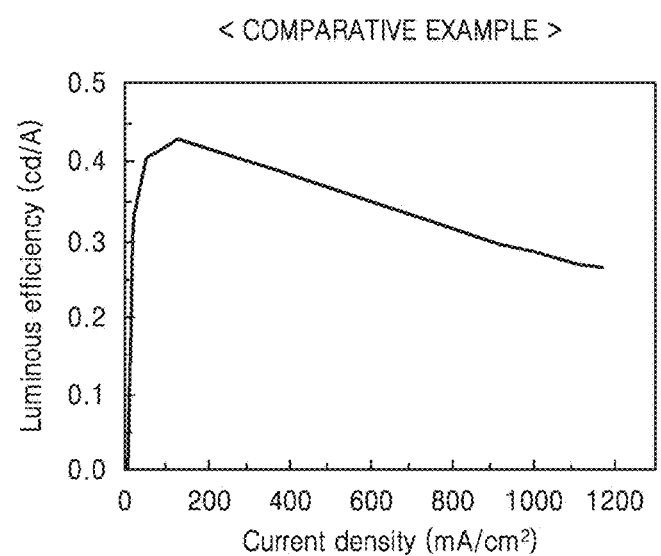
Figure 51:
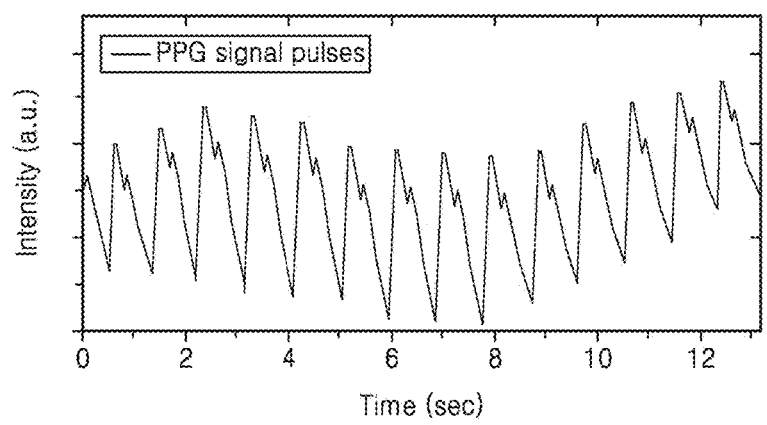
Figure 52:
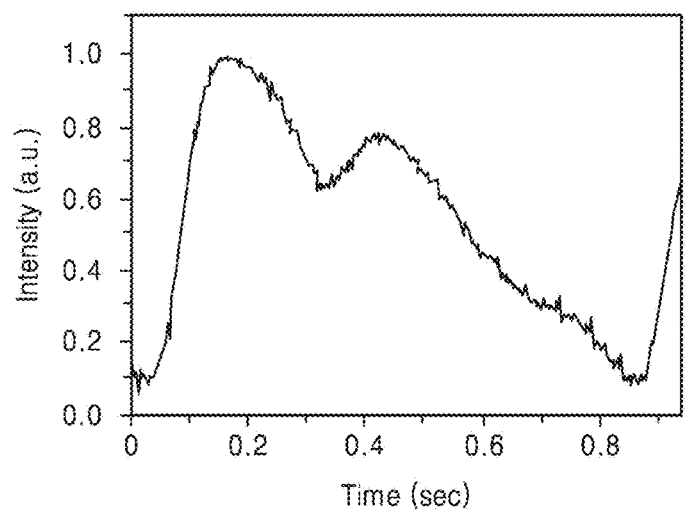
Figure 53:
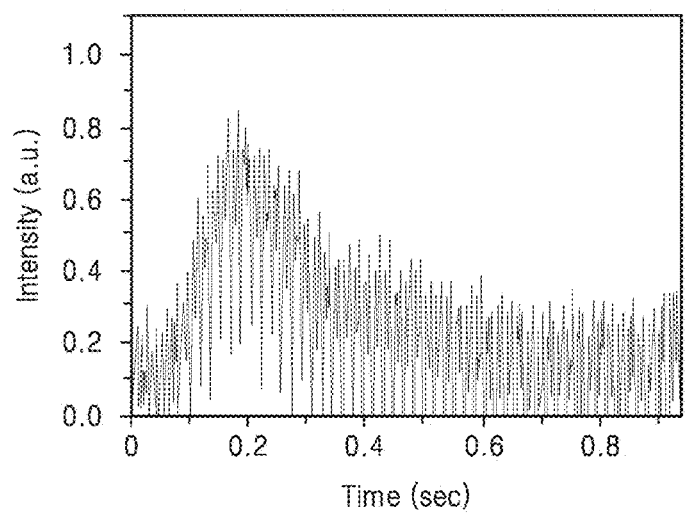
Figure 54:
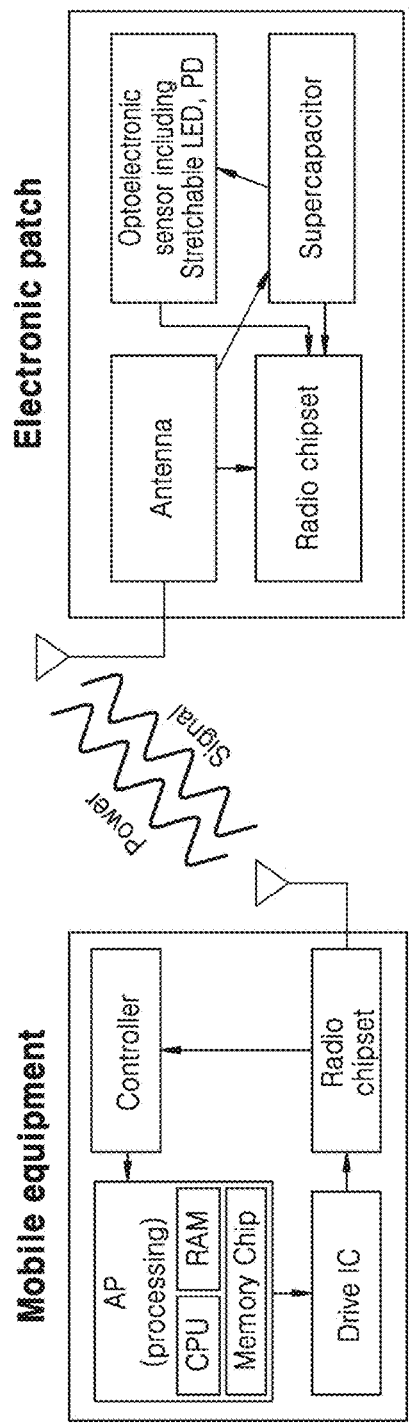
Figure 55:
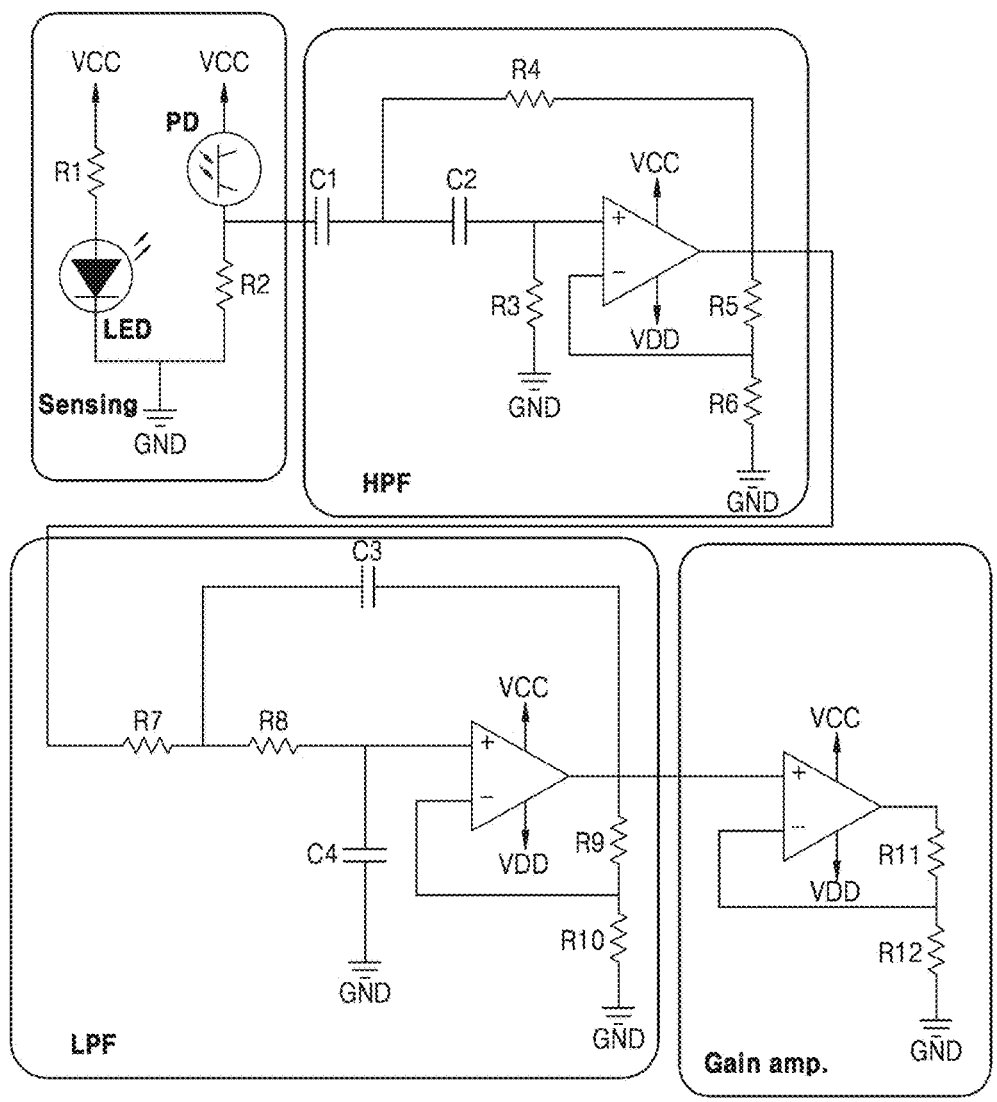

These and/or other aspects will become apparent and more readily appreciated from the following description of non-limiting embodiments, taken in conjunction with the accompanying drawings. The drawings are not necessarily to scale, emphasis instead being placed upon illustrating principles of inventive concepts. In the drawings:

FIG. 1 is a cross-sectional view illustrating a stretchable optoelectronic device according to example embodiments;

FIG. 2 is a cross-sectional view illustrating a stretchable optoelectronic device according to example embodiments;

FIG. 3 is a cross-sectional view illustrating a stretchable optoelectronic device according to example embodiments;

FIG. 4 is a cross-sectional view illustrating a stretchable optoelectronic device according to example embodiments;

FIG. 5 is a cross-sectional view illustrating a stretchable optoelectronic device according to example embodiments;

FIG. 6 is a cross-sectional view illustrating a stretchable optoelectronic device according to example embodiments;

FIG. 7 is a cross-sectional view illustrating a stretchable optoelectronic device according to example embodiments;

FIG. 8 is a cross-sectional view illustrating a stretchable optoelectronic device according to example embodiments;

FIG. 9 is a cross-sectional view illustrating a stretchable optoelectronic device according to example embodiments;

FIG. 10 is a cross-sectional view illustrating a stretchable optoelectronic device according to example embodiments;

FIG. 11 is a cross-sectional view illustrating a stretchable optoelectronic device according to example embodiments;

FIG. 12 is a cross-sectional view illustrating a stretchable optoelectronic device according to example embodiments;

FIG. 13 is a cross-sectional view illustrating a stretchable optoelectronic device according to example embodiments;

FIG. 14 is a cross-sectional view illustrating a stretchable optoelectronic device according to example embodiments;

FIG. 15 is a cross-sectional view simplifying the stretchable optoelectronic device of FIG. 14, according to example embodiments;

FIG. 16 is a cross-sectional view illustrating a quantum dot (QD)-containing layer that may be included in any of the stretchable optoelectronic devices of FIGS. 1 to 15, according to example embodiments;

FIGS. 17A through 17F are cross-sectional views for explaining a method of manufacturing a stretchable optoelectronic device, according to example embodiments;

FIG. 18 is a cross-sectional view for explaining a method of manufacturing a stretchable optoelectronic device, according to example embodiments;

FIGS. 19A through 19D are cross-sectional views for explaining a method of manufacturing a stretchable optoelectronic device, according to example embodiments;

FIG. 20 is a cross-sectional view for explaining a method of manufacturing a stretchable optoelectronic device, according to example embodiments;

FIGS. 21A through 21C are cross-sectional views for explaining a method of manufacturing a stretchable optoelectronic device, according to example embodiments;

FIG. 22 is a cross-sectional view for explaining a method of manufacturing a stretchable optoelectronic device, according to example embodiments;

FIGS. 23A through 23D are cross-sectional views for explaining a method of manufacturing a stretchable optoelectronic device, according to example embodiments;

FIG. 24 is a cross-sectional view for explaining a method of manufacturing a stretchable optoelectronic device, according to example embodiments;

FIG. 25 is a plan image illustrating a wavy structure of a graphene/poly(3,4-ethylenedioxythiophene) (PEDOT) stack structure that may be applied to a stretchable/foldable optoelectronic device, according to example embodiments;

FIG. 26 is a graph illustrating a relationship between a thickness of a PEDOT layer of a graphene/PEDOT stack structure and a wavelength of a wavy structure, according to example embodiments;

FIGS. 27A through 27F are plan images illustrating a morphology while a graphene/PEDOT stack structure is stretched, according to example embodiments;

FIG. 28 is a graph illustrating a relationship between strain of a graphene/PEDOT stack structure having a wavy structure and a sheet resistance (Ω/sq), according to example embodiments;

FIG. 29 is a graph illustrating a result obtained after measuring a transmittance of a polydimethylsiloxane (PDMS)/graphene/PEDOT stack structure having a wavy structure, according to example embodiments;

FIGS. 30A through 30D are plan images illustrating a wavy structure of a quantum dot (QD) layer that is transfer-printed onto a prestrained PDMS substrate, according to example embodiments;

FIG. 31 is a graph illustrating a relationship between a thickness of a QD layer that is transfer-printed onto a prestrained PDMS substrate and a wavelength of a wavy structure, according to example embodiments;

FIGS. 32A through 32D are plan images illustrating a morphology while stretching a polyethylene naphthalate (PEN)/graphene stack structure that is formed on an elastic substrate (e.g., an ECOFLEX® substrate (platinum-catalyzed silicones made by Smooth-On Inc.)), according to example embodiments;

FIGS. 33A and 33B are plan images illustrating a uniaxial wavy structure and a multiaxial wavy structure of an optoelectronic device, according to example embodiments;

FIGS. 34A and 34B are images illustrating an operation of a stretchable/foldable optoelectronic device (e.g., a light-emitting device), according to example embodiments;

FIG. 35 is an image illustrating a case where the optoelectronic device of FIGS. 34A and 34B is bent and folded, according to example embodiments;

FIGS. 36A through 36C are images illustrating a case where a stretchable/foldable optoelectronic device (e.g., a light-emitting device) is stretched, according to example embodiments;

FIG. 37 is a graph illustrating an electroluminescence (EL) spectrum of a stretchable/foldable optoelectronic device (e.g., a light-emitting device), according to example embodiments, FIG. 38 is a graph illustrating voltage-current density characteristics of a stretchable/foldable optoelectronic device (e.g., a light-emitting device), according to example embodiments;

FIG. 39 is a graph illustrating voltage-brightness characteristics of a stretchable/foldable optoelectronic device (e.g., a light-emitting device), according to example embodiments;

FIG. 40 is a graph illustrating current density-luminous efficiency characteristics of a stretchable/foldable optoelectronic device (e.g., a light-emitting device), according to example embodiments;

FIG. 41 is an image illustrating an optoelectronic device (e.g., a light-emitting device) that is directly formed on a prestrained PDMS substrate without using a plastic material layer such as a PEN layer, according to example embodiments;

FIG. 42 is a graph illustrating voltage-current density characteristics of the optoelectronic device of FIG. 41, according to example embodiments;

FIG. 43 is a graph illustrating voltage-brightness characteristics of the optoelectronic device of FIG. 41, according to example embodiments;

FIG. 44 is an image illustrating an optoelectronic device (e.g., a light-emitting device) that is manufactured by using a plastic material layer (e.g., a PEN layer) on a prestrained PDMS substrate, according to example embodiments;

FIGS. 45A through 45C are images illustrating a case where the optoelectronic device of FIG. 44 is stretched, according to example embodiments;

FIG. 46 is an image illustrating a case where the optoelectronic device of FIG. 44 is bent, according to example embodiments;

FIG. 47 is a graph illustrating voltage-current density characteristics of a stretchable/foldable optoelectronic device (e.g., a light-emitting device), according to example embodiments;

FIG. 48 is a graph illustrating voltage-brightness characteristics of a stretchable/foldable optoelectronic device (e.g., a light-emitting device), according to example embodiments;

FIG. 49 is a graph illustrating current density-luminous efficiency characteristics of a stretchable/foldable optoelectronic device (e.g., a light-emitting device), according to example embodiments;

FIG. 50 is a graph illustrating current density-luminous efficiency characteristics of a light-emitting device, according to a comparative example;

FIG. 51 is a graph illustrating a result obtained after measuring a heart rate of a subject (e.g., a person) by using a photoplethysmography (PPG) sensor using a stretchable/foldable optoelectronic device (e.g., a light-emitting device), according to example embodiments;

FIG. 52 is a graph illustrating a pulse corresponding to one cycle among PPG signal pulses that are measured by using a PPG sensor using a stretchable/foldable optoelectronic device (e.g., a light-emitting device), according to example embodiments;

FIG. 53 is a graph illustrating a pulse corresponding to one cycle among PPG signal pulses that are measured by using a PPG sensor using a light-emitting device, according to a comparative example;

FIG. 54 is a system diagram of a sensor system according to example embodiments; and FIG. 55 is a circuit diagram of a sensor system according to example embodiments.

DETAILED DESCRIPTION

Example embodiments will now be described more fully with reference to the accompanying drawings, in which some example embodiments are shown. Example embodiments, may, however, be embodied in many different forms and should not be construed as being limited to the embodiments set forth herein; rather, these example embodiments are provided so that this disclosure will be thorough and complete, and will fully convey the scope of example embodiments of inventive concepts to those of ordinary skill in the art. In the drawings, the thicknesses of layers and regions are exaggerated for clarity. Like reference characters and/or numerals in the drawings denote like elements, and thus their description may be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements or layers should be interpreted in a like fashion (e.g., "between" versus "directly between," "adjacent" versus "directly adjacent," "on" versus "directly on"). As used herein the term "and/or" includes any and all combinations of one or more of the associated listed items.

It will be understood that, although the terms "first", "second", etc. may be used herein to describe various elements, components, regions, layers and/or sections. These elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof. Expressions such as "at least one of," when preceding a list of elements, modify the entire list of elements and do not modify the individual elements of the list.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

FIG. 1 is a cross-sectional view illustrating a stretchable optoelectronic device 100 according to example embodiments. The stretchable optoelectronic device 100 may be a foldable optoelectronic device. Hereinafter, the stretchable optoelectronic device 100 is referred to as a 'stretchable device'.

Referring to FIG. 1, the stretchable device 100 may include a substrate S10 that is elastic. The substrate S10 may include an elastomeric polymer and may be stretchable. The elastomeric polymer may be elastomeric rubber. The stretchable device 100 may include an optoelectronic device portion D10 that is disposed on the substrate S10. The optoelectronic device portion D10 may be any one from among a light-emitting device portion, a photovoltaic device portion, and a photo-detecting device portion. The optoelectronic device portion D10 may have a multi-layer structure including a graphene layer and a light-emitting layer or a light-sensing layer. In FIG. 1, for ease of description, an example is described where the optoelectronic device portion D10 may have a multi-layer structure including a graphene layer and a quantum dot (QD)-containing layer, but example embodiments are not limited thereto. Also, the optoelectronic device portion D10 may have a wavy structure. The optoelectronic device portion D10 may be stretchable due to the wavy structure thereof. The wavy structure may be referred to as a buckled structure or a corrugated structure.

When the optoelectronic device portion D10 is a light-emitting device portion, the QD-containing layer (e.g., a QD layer) may be used as a 'light-emitting layer (active layer)'. Alternatively, the light-emitting layer LE11 may include a self-emissive material formed of transition metal dichalcogenide (TMDC). QDs are advantageous in that QDs have high color purity, high quantum yield, high stability, and self light-emitting characteristics, colors of light are easily adjusted by changing the sizes of QDs, and a solution process may be used. Accordingly, QDs may be applied to next-generation large-area/high-quality display devices. However, since it is difficult for the QD layer or the QD-containing layer itself to be stretchable like elastomeric rubber, it may not be easy to form a stretchable device including the QD layer or the QD-containing layer. However, according to example embodiments, the stretchable device 100, including the QD-containing layer, may be realized by disposing the optoelectronic device portion D10, including the QD-containing layer, on the substrate S10 that is elastic and forming the wavy structure in the optoelectronic device portion D10. Since a surface of the QD-containing layer may be a 'light-emitting surface' and the light-emitting surface may have the wavy structure, the stretchable device 100 of example embodiments may be a device having a stretchable or foldable light-emitting surface.

The graphene layer of the optoelectronic device portion D10 may be used as an electrode. For example, the graphene layer may be used as an anode. Since graphene has a high light transmittance and limits (and/or prevents) penetration of oxygen or moisture, graphene may protect the optoelectronic device portion D10 from oxygen or moisture without cutting off light. Also, graphene has a very small thickness, excellent flexibility, and a high strength. Accordingly, graphene may be stretchable or bendable in the wavy structure. In particular, the graphene may maintain its own characteristics without being damaged by repeated stretching or an extremely small bending radius of about 150 nm or less. Also, since graphene has a relatively high work function and excellent electrical conductivity (that is, a low electrical resistance), graphene may be used as an electrode (e.g., an anode). When the optoelectronic device portion D10 includes graphene and QDs, the stretchable device 100 may be referred to as a graphene-QD-based device or a hybrid graphene-QD-based device.

The elastomeric polymer of the substrate S10 may be a material having a Poisson's ratio that is equal to or greater than 0.4 or 0.45. For example the elastomeric polymer may have a Poisson's ratio that is a range from 0.4 to 0.5 and/or 0.45 to 0.5, but example embodiments are not limited thereto. The term 'Poisson's ratio' refers to a ratio of transverse strain to axial strain when normal stress is applied to a material. When a Poisson's ratio of a polymer is equal to or greater than 0.4, the polymer may be easily stretched, like elastomeric rubber. In example embodiments, the elastomeric polymer of the substrate S10 may include at least one selected from the group consisting of silicon-based polymer, polyurethane (PU), polyurethane acrylate (PUA), acrylate polymer, and acrylate terpolymer. The silicon-based polymer may include at least one selected from the group consisting of, for example, polydimethylsiloxane (PDMS), polyphenyl-methylsiloxane, and hexamethyldisiloxane. Also, ECOFLEX® (platinum-catalyzed silicones made by Smooth-On Inc.) may be used as the silicon-based polymer. The afore-described materials may each have a Poisson's ratio that is equal to or greater than 0.4. For example, a Poisson's ratio of the PDMS may be 0.48 and a Poisson's ratio of the PU may be 0.5. The afore-described specific materials of the substrate S10 are examples and other elastomeric polymers may be used.

Since the substrate S10 may be stretchable due to the elastomeric polymer and the optoelectronic device portion D10 that is formed on a surface of the substrate S10 may be stretchable due to the wavy structure thereof, the stretchable device 100 may be stretchable (extensible). Also, the stretchable device 100 may be a foldable device.

According to example embodiments, a capping layer that is elastic may be further disposed on the optoelectronic device portion D10 of FIG. 1, as shown in FIG.

Referring to FIG. 2, a stretchable device 100-1 may further include a capping layer C10 that is elastic and formed on the optoelectronic device portion D10. The optoelectronic device portion D10 may be disposed between the substrate S10 and the capping layer C10. The capping layer C10 may be referred to as an 'encapsulation layer'. The capping layer C10 may be formed of a material that is similar to or the same as that of the substrate S10. That is, the capping layer C10 may include an elastomeric polymer (e.g., elastomeric rubber) and may be stretchable. The elastomeric polymer of the capping layer C10 may be the same as or different from the elastomeric polymer of the substrate S10. For example, the elastomeric polymer of the capping layer C10 may include at least one selected from the group consisting of PU, PUA, acrylate polymer, acrylate terpolymer, and silicon-based polymer. The silicon-based polymer may include at least one selected from the group consisting of, for example, PDMS, polyphenyl-methylsiloxane, and hexamethyldisiloxane. Also, ECOFLEX® (platinum-catalyzed silicones made by Smooth-On Inc.) may be used as the silicon-based polymer. However, the afore-described specific materials of the capping layer C10 are examples and other elastomeric polymers may be used.

As shown in FIG. 2, when the optoelectronic device portion D10 is disposed between the substrate S10 that is elastic and the capping layer C10 that is elastic, the optoelectronic device portion D10 may be located on or around a mechanical neutral plane (MNP). MNP refers to an area (plane) where even mechanical deformation of the stretchable device 100-1 does not produce stress. When the optoelectronic device portion D10 is located on the MNP, it means that even when the stretchable device 100-1 is deformed, no or little tensile strain or stress is applied to the optoelectronic device portion D10. Accordingly, when the optoelectronic device portion D10 is located on or around the MNP, damage to or deterioration in characteristics of the optoelectronic device portion D10 due to deformation (e.g., tensile deformation) of the stretchable device 100-1 may be limited (and/or prevented or minimized).

A position of the MNP may vary depending on a material and a thickness of the substrate S10, a material and a thickness of the capping layer C10, and a stack structure and a material of the optoelectronic device portion D10. In other words, a position of the MNP may be appropriately controlled by changing a material and a thickness of the substrate S10 and a material and a thickness of the capping layer C10. Also, when an additional material layer is disposed between the substrate S10 and the optoelectronic device portion D10 or an additional material layer is disposed between the optoelectronic device portion D10 and the capping layer C10, a position of the MNP may be changed. In example embodiments, the MNP may be located in an active layer (e.g., a light-emitting layer or light-sensing layer) of the optoelectronic device portion D10. The active layer may be the 'QD-containing layer'. Accordingly, damage to or deterioration in characteristics of the active layer due to deformation of the stretchable device 100-1 may be limited (and/or prevented or minimized).

In addition, the capping layer C10 of FIG. 2 may function as a protective layer that protects the optoelectronic device portion D10 from moisture and oxygen. Also, the capping layer C10 may be a transparent layer.

According to example embodiments, a 'plastic material layer' may be further disposed on a surface of the optoelectronic device portion D10. The plastic material layer may be disposed on a bottom surface or a top surface of the optoelectronic device portion D10, as shown in FIGS. 3 and 4.

Referring to FIG. 3, a stretchable device 100-2 may further include a plastic material layer P10 that is disposed between the substrate S10 and an optoelectronic device portion D10a. In this case, the plastic material layer P10 may be disposed on a bottom surface of the optoelectronic device portion D10a. With the capping layer C10 disposed on the optoelectronic device portion D10a, the optoelectronic device portion D10a may be disposed between the plastic material layer P10 and the capping layer C10. The optoelectronic device portion D10a may have a configuration that is substantially the same as that of the optoelectronic device portion D10 of FIGS. 1 and 2.

The plastic material layer P10 may have a Poisson's ratio that is less than that of the elastomeric polymer of each of the substrate S10 and the capping layer C10. For example, a Poisson's ratio of the plastic material layer P10 may be less than 0.45 or 0.4. For example, a Poisson's ratio of the plastic material layer P10 may be in a range of 0.33 to 0.45 and/or a range of 0.35 to 0.4, but is not limited thereto. In other cases, a Poisson's ratio of the plastic material layer P10 may be less than about 0.33 or 0.3. Also, a Young's modulus of the plastic material layer P10 may be greater than that of the elastomeric polymer of each of the substrate S10 and the capping layer C10. For example, the plastic material layer P10 may include at least one selected from the group consisting of polyethylene naphthalate (PEN), polyimide (PI), and polyethylene terephthalate (PET). A thickness of the plastic material layer P10 may range, for example, from about 0.5 μm to about 100 μm or from about 0.5 μm to about 30 μm. A wavelength (e.g., an average wavelength) and an amplitude (e.g., an average amplitude) of a wavy structure of the optoelectronic device portion D10a may vary depending on a thickness of the plastic material layer P10. As a thickness of the plastic material layer P10 decreases, a wavelength and amplitude of the wavy structure may decrease. Accordingly, as a thickness of the plastic material layer P10 decreases, strain (e.g., tensile strain) of the optoelectronic device portion D10a may increase.

The plastic material layer P10 may be a layer that is used in a process of manufacturing the stretchable device 100-2. Also, as described above, strain of the optoelectronic device portion D10a, that is, strain of the stretchable device 100-2, may be adjusted by using the plastic material layer P10.

According to example embodiments, as shown in FIG. 4, the plastic material layer P10 may be disposed on a top surface of an optoelectronic device portion D10b. In this case, the optoelectronic device portion D10b may be disposed between the substrate S10 and the plastic material layer P10. The capping layer C10 may be disposed on the plastic material layer P10. Accordingly, the plastic material layer P10 may be disposed between the optoelectronic device portion D10b and the capping layer C10. Reference numeral 100-3 denotes a 'stretchable device (stretchable optoelectronic device)'.

The optoelectronic device portion D10b of FIG. 4 may have a structure (that is, an inverted structure) obtained by vertically overturning the optoelectronic device portion D10a of FIG. 3. For example, a QD-containing layer may be disposed over a graphene layer in the optoelectronic device portion D10a of FIG. 3, whereas a QD-containing layer may be disposed under a graphene layer in the optoelectronic device portion D10b of FIG. 4.

Although not shown in FIG. 4, an adhesive layer may be further disposed between the substrate S10 and the optoelectronic device portion D10b. The adhesive layer may be an organic adhesive layer. The adhesive layer may be formed of a material that is substantially the same as that of the capping layer C10. For example, the adhesive layer may include at least one selected from the group consisting of PU, PUA, acrylate polymer, acrylate terpolymer, and silicon-based polymer. The silicon-based polymer may include at least one selected from the group consisting of, for example, PDMS, polyphenyl-methylsiloxane, and hexamethyldisiloxane.

Since each of the optoelectronic device portions D10a and D10b of FIGS. 3 and 4 is disposed between the substrate S10 and the capping layer C10, each of the optoelectronic device portions D10a and D10b may be located on or around an MNP. A QD-containing layer of each of the optoelectronic device portions D10a and D10b may be located on or around the MNP. The MNP has already been described and thus a repeated explanation thereof will not be given.

A wavy structure of each of the optoelectronic device portions D10, D10a, and D10b of FIGS. 1 through 4 may have a relatively uniform waveform. The wavy structure may have a desired (and/or alternatively predetermined) wavelength and a desired (and/or alternatively predetermined) amplitude. An average wavelength of the wavy structure of each of the optoelectronic device portions D10, D10a, and D10b may range from about 3 µm to about 3 mm or from about 10 µm to about 2 mm, and an average amplitude of each of the optoelectronic device portions D10, D10a, and D10b may range from about 50 nm to about 2 mm or from about 100 nm to about 1 mm. The average wavelength and the average amplitude of the wavy structure may be values measured when the optoelectronic device portions D10, D10a, and D10b are not stretched, that is, are unstretched. As the average wavelength of the wavy structure decreases, strain (e.g., tensile strain) of each of the optoelectronic device portions D10, D10a, and D10b may increase. In FIGS. 3 and 4, a wavelength (e.g., an average wavelength) and an amplitude (e.g., an average amplitude) of the wavy structure may be adjusted according to a thickness of the plastic material layer P10.

Each of the stretchable devices 100, 100-1, 100-2, and 100-3 of FIGS. 1 through 4 may have strain (tensile strain) that is equal to or greater than about 5% or about 10%. Strain (e.g., tensile strain) of each of the stretchable devices 100, 100-1, 100-2, and 100-3 may be equal to or greater than about 50% or about 100%. Even when each of the stretchable devices 100, 100-1, 100-2, and 100-3 is stretched until the wavy structure of each of the optoelectronic device portions D10, D10a, and D10b becomes a planar structure, electrical and optical characteristics of each of the optoelectronic device portions D10, D10a, and D10b may be stably maintained. That is, even when the wavy structure is stretched, since no cracks occur and a fine structure is not changed until the wavy structure becomes a planar structure, electrical and optical characteristics of each optoelectronic device portion may be maintained constant. Also, each of the stretchable devices 100, 100-1, 100-2, and 100-3 may be bent to a bending radius of about 1 mm or less. A bending radius of each of the stretchable devices 100, 100-1, 100-2, and 100-3 may be equal to or less than about 0.5 mm or about 0.1 mm. Accordingly, each of the stretchable devices 100, 100-1, 100-2, and 100-3 may be a foldable device. In particular, as shown in FIGS. 2 through 4, when each of the optoelectronic device portions D10, D10a, and D10b is embedded between the substrate S10 that is elastic and the capping layer C10 that is elastic and each of the stretchable devices 100-1, 100-2, and 100-3 is physically deformed, damage to or deterioration in characteristics of each of the optoelectronic device portions D10, D10a, and D10b may be (limited and/or prevented). Accordingly, according example embodiments, a stretchable/foldable optical apparatus (electronic apparatus) having excellent characteristics and stability may be realized.

Although a simple structure of each of the optoelectronic device portions D10, D10a, and D10b has been described in FIGS. 1 through 4, a detailed structure of each of the optoelectronic device portions D10, D10a, and D10b and a stretchable/foldable optoelectronic device including the same will now be explained in detail with reference to FIGS. 5 through 12.

FIG. 5 is a cross-sectional view illustrating a stretchable optoelectronic device 100A according to example embodiments. The stretchable optoelectronic device 100A may be a foldable optoelectronic device. Hereinafter, the stretchable optoelectronic device 100A is referred to as a 'stretchable device'.

Referring to FIG. 5, the stretchable device 100A may include a substrate S11 that is elastic and an optoelectronic device portion D11 that is disposed on the substrate S11. The optoelectronic device portion D11 may include a light-emitting layer LE11 (and/or a light-sensing layer) between a first electrode E11 and a second electrode E21. For example, the optoelectronic device portion D11 may include a graphene layer and a QD-containing layer and may have a wavy structure. The optoelectronic device portion D11 may be stretchable due to the wavy structure thereof. The stretchable device 100A may further include a plastic material layer P11 that is disposed between the substrate S11 and the optoelectronic device portion D11. The substrate S11, the plastic material layer P11, and the optoelectronic device portion D11 may respectively correspond to the substrate S10, the plastic material layer P10, and the optoelectronic device portion D10a of FIG. 3.

The optoelectronic device portion D11 may be at least one selected from the group consisting of a light-emitting device portion, a photovoltaic device portion, and a photo-detecting device portion. A case where the optoelectronic device portion D11 is a light-emitting device portion is shown in FIG. 5. In this case, the optoelectronic device portion D11 may include a first electrode E11, a light-emitting layer LE11, and a second electrode E21 that are sequentially disposed from the substrate 811. One of the first and second electrodes E11 and E21 may be an anode, and the other may be a cathode. For example, the first electrode E11 may be an anode, and the second electrode E21 may be a cathode. An anode from among the first and second electrodes E11 and E21, for example, the first electrode E11, may include a graphene layer. Reference character GP denotes 'graphene'. The graphene layer may have a single-layer structure including a single graphene layer or a multi-layer structure including graphene layers (e.g., less than about 100 or about 10 graphene layers). The light-emitting layer LE11 that is disposed between the first and second electrodes E11 and E21 may include a QD-containing layer. Reference character QD denotes a 'quantum dot'. For example, the light-emitting layer LE11 may include a QD layer. Alternatively, the light-emitting layer LE11 may include a self-emissive material formed of transition metal dichalcogenide (TMDC). The optoelectronic device portion D11 may further include a hole transport layer HTL11 that is disposed between the first electrode E11 and the light-emitting layer LE11 and an electron transport layer ETL11 that is disposed between the second electrode E21 and the light-emitting layer LE11. Also, the optoelectronic device portion D11 may further include a hole injection layer HIL11 that is disposed between the first electrode E11 and the hole transport layer HTL11. Although not shown in FIG. 5, the optoelectronic device portion D11 may further include an electron injection layer that is disposed between the second electrode E21 and the electron transport layer ETL11.

The first electrode E11 may include the graphene layer and may have a relatively high work function. The graphene layer of the first electrode E11 may be an undoped layer, or may be a layer doped with a p-type dopant if necessary. That is, if necessary, the graphene layer of the first electrode E11 may be p-doped. Due to the p-doping, a work function of the graphene layer may be increased and an electrical resistance thereof may be reduced. For example, $AuCl_3$ or $HNO_3$ may be used as a source of the p-type dopant.

The second electrode E21 may have a relatively low work function. For example, a work function of the second electrode E21 may range from about 3.4 eV to about 4.2 eV. The second electrode E21 may include a metal or a metal compound, but is not limited thereto. Also, the second electrode E21 may have a single-layer or multi-layer structure. For example, the second electrode E21 may include an aluminum (Al-lithium (Li) alloy, Al, lithium fluoride (LiF)/Al, silver (Ag), calcium (Ca), Ca/Al, or Ca/Ag. The LiF/Al refers to a multi-layer structure including a LiF layer and an Al layer that is formed on the LiF layer. The same applies to Ca/Al and Ca/Ag. The second electrode E21 may be formed of graphene that is doped with an n-type dopant. Since a work function of graphene may be reduced due to an n-type dopant, an n-doped graphene layer may be used as the second electrode E21. Also, the second electrode E21 may include metal nanowires, carbon nanotubes (CNTs), or graphene flakes. For example, the second electrode E21 may have a structure including a network of a plurality of metal nanowires, a plurality of CNTs, or a plurality of graphene flakes. The network structure may be embedded in a desired (and/or alternatively predetermined) polymer material layer. Ag nanowires may be used as the metal nanowires. The metal nanowires or the CNTs may be transparent. Accordingly, the second electrode E21 may be transparent and may be used to manufacture a transparent device (e.g., a transparent light-emitting device). However, the afore-described specific materials of the second electrode E21 are examples and other various materials may be used.

The electron transport layer ETL11 may include an n-type organic semiconductor and/or an n-type inorganic semiconductor. The n-type inorganic semiconductor may be an oxide or a non-oxide, and the n-type organic semiconductor may be a monomer or a polymer. For example, the n-type inorganic semiconductor may be an n-type oxide semiconductor (e.g., $TiO_x$, $ZnO_x$, or $ZrO_x$) an n-type non-oxide semiconductor such as n-GaN, or an N-type transition metal dichalcogenide (TMDC) (e.g., $MoS_2$, $MoSe_2$, $MoTe_2$, $WSe_2$, $WTe_2$). The n-type inorganic semiconductor (e.g., $TiO_x$) may be combined with a desired (and/or alternatively predetermined) polymer to form the electron transport layer ETL11. The n-type organic semiconductor may include a monomer-based organic material such as $Alq_3$, TAZ, TPBi, or BPhen or may include a polymer-based organic material such as $P_3CN_4HT$.

Chemical names of the $Alq_3$, TAZ, TPBi, BPhen, and $P_3CN_4HT$ are as follows:
  $Alq_3$: tris-(8-hydroxyquinilone)aluminum
  TAZ: 3-(4-biphenyl)-4-phenyl-5-(4-tert-butylphenyl)-1,2,4-triazole
  TPBi: 2,2,2-(1,3,5-benzinetriyl)-tris(1-phenyl-1-H-benzimidazole)
  BPhen: 4,7-diphenyl-1,10-phenanthroline
  $P_3CN_4HT$: poly(3-cyano-4-hexylthiophene)

However, the afore-described specific materials of the electron transport layer ETL11 are examples and other various materials may be used for the electron transport layer ETL11. The electron transport layer ETL11 may be formed by using sol-gel, spray coating, spin coating, blade coating, printing, or deposition.

The hole transport layer HTL11 may include a p-type organic semiconductor and/or a p-type inorganic semiconductor. The p-type inorganic semiconductor may be an oxide or a non-oxide, and the p-type organic semiconductor may be a monomer or a polymer. For example, the p-type inorganic semiconductor may be a p-type oxide semiconductor such as $MoO_x$, $NiO_x$, $V_xO_y$, or $Rh_xO_y$, a p-type non-oxide semiconductor such as p-GaN, a p-type transition metal dichalcogenide (TMDC) (e.g., $WS_2$, $ZrS_2$, $ZrSe_2$, $HfS_2$, $HfSe_2$, $NbSe_2$). The p-type inorganic semiconductor may be combined with a desired (and/or alternatively predetermined) polymer to form the hole transport layer HTL11. The p-type organic semiconductor may include a monomer-based organic material such as NPD or TPD, or may include a polymer-based organic material such as TFB, PFB, or F8T2. Chemical names of the NPD, TPD, TFB, PFB, and $F_8T_2$ are as follows:
  NPD: N,N'-diphenyl-N,N'-bis(1-naphthyl)-1,1'biphenyl-4,4diamine
  TPD: N,N'-bis(3-methyphenyl)-N,N'-diphenylbenzidine
  TFB: poly(9,9-dioctylfluorene-co-N-(4-butylphenyl)diphenylamine)
  PFB: poly(9,9-dioctylfluorene-co-bis-N,N-phenyl-1,4-phenylenediamine
  $F_8T_2$: poly(9,9-dioctylfluorene-co-bithiophene)

However, the afore-described specific materials of the hole transport layer HTL11 are examples and other various materials may be used for the hole transport layer HTL11. Like the electron transport layer ELT11, the hole transport layer HTL11 may be formed by using sol-gel, spray coating, spin coating, blade coating, printing, or deposition.

The hole injection layer HIL11 may include, for example, poly(3,4-ethylenedioxythiophene) (PEDOT) or poly(N-vinylcarbazole).

(PVK). The PEDOT may have a high transmittance and may increase an electrical conductivity of the graphene layer of the first electrode E11 when the PEDOT contacts the graphene layer of the first electrode E11. When an electrical conductivity of the hole injection layer HIL11 is high, the hole injection layer HTL11 may be considered as a part of an electrode (e.g., an anode). The afore-described specific materials of the hole injection layer HIL11 are examples and other various materials may be used for the hole injection layer HIL11. Also, the hole injection layer HIL11 may not be provided. In this case, the hole transport layer HTL11 may function as the hole injection layer HIL11.

A capping layer that is elastic may be further disposed on the optoelectronic device portion D11 of FIG. 5, as shown in FIG. 6.

Referring to FIG. 6, a stretchable device 100B may further include a capping layer C11 that is disposed on the optoelectronic device portion D11. The capping layer C11 may be substantially the same as the capping layer C10 of FIGS. 2 through 4. Since the capping layer C11 is provided, the optoelectronic device portion D11 of the stretchable device 100B may be located on or around an MNP. For example, the light-emitting layer LE11 of the optoelectronic device portion D11 may be located on or around the MNP. The MNP has already been described with reference to FIGS. 2 through 4, and thus a repeated explanation thereof will not be given.

According to example embodiments, an order in which constituent layers of the optoelectronic device portion D11 of FIGS. 5 and 6 are arranged may be vertically inverted. That is, an inverted structure obtained by vertically overturning the optoelectronic device portion D11 of FIGS. 5 and 6 may be applied to the substrate S11. In this case, a position of the plastic material layer P11 may also be changed, as shown in FIGS. 7 and 8.

FIG. 7 is a cross-sectional view illustrating a stretchable optoelectronic device (hereinafter, referred to as a stretchable device) 100c according to example embodiments.

Referring to FIG. 7, an optoelectronic device portion D12 may be disposed on a substrate S12 that is elastic. A plastic material layer P12 may be disposed on the optoelectronic device portion D12. Accordingly, the optoelectronic device portion D12 may be disposed between the substrate S12 and the plastic material layer P12. The optoelectronic device portion D12 may have an inverted structure obtained by vertically overturning the optoelectronic device portion D11 of FIG. 5. That is, the optoelectronic device portion D12 may include a second electrode E22, an electron transport layer ETL12, a light-emitting layer LE12, a hole transport layer HTL12, a hole injection layer HIL12, and a first electrode E12 that are sequentially disposed on the substrate S12 in this order. In this case, the second electrode E22 may be referred to as a 'first electrode', and the first electrode E12 may be referred to as a 'second electrode'. The first electrode E12 may be an anode, and the second electrode E22 may be a cathode. The first electrode E12 may include a graphene layer, and the light-emitting layer LE12 may include a QD-containing layer. The plastic material layer P12 may be disposed to contact the first electrode E12. When the first electrode E12 includes a graphene layer, the plastic material layer P12 may contact the graphene layer.

The stretchable device 100C according to example embodiments may further include an adhesive layer B12 that is disposed between the substrate S12 and the optoelectronic device portion D12. The adhesive layer B12 may be an organic adhesive layer. The adhesive layer B12 may be formed of a material that is substantially the same as that of the capping layer C11 of FIG. 6. For example, the adhesive layer B12 may include at least one selected from the group consisting of PU, PUA, acrylate polymer, acrylate terpolymer, and silicon-based polymer. The silicon-based polymer may include at least one selected from the group consisting of, for example, PDMS, polyphenyl-methylsiloxane, and hexamethyldisiloxane. The above-described materials of the adhesive layer B12 are non-limiting examples and other various materials may be used.

A capping layer that is elastic may be further disposed on the plastic material layer P12 of FIG. 7, as shown in FIG. 8.

Referring to FIG. 8, a stretchable device 100D may further include a capping layer C12 that is disposed on the plastic material layer P12. The capping layer C12 may be substantially the same as the capping layer C10 of FIGS. 2 through 4. Since the capping layer C12 is provided, the optoelectronic device portion D12 may be located on or around an MNP. For example, the light-emitting layer LE12 of the optoelectronic device portion D12 may be located on or around the MNP.

Although the plastic material layers P11 and P12 are respectively disposed on surfaces of the optoelectronic device portions D11 and D12 in FIGS. 5 through 8, the plastic material layers P11 and P12 may not be used if necessary, as shown in FIGS. 9 through 12.

FIG. 9 is a cross-sectional view illustrating a stretchable optoelectronic device 100E according to example embodiments. The stretchable optoelectronic device 100E may be a foldable optoelectronic device. Hereinafter, the stretchable optoelectronic device 100E is referred to as a 'stretchable device'.

Referring to FIG. 9, an optoelectronic device portion D13 may be disposed on a substrate S13 that is elastic. The optoelectronic device portion D13 may have a stack structure that is substantially the same as that of the optoelectronic device portion D11 of FIG. 5. That is, the optoelectronic device portion D13 may include a first electrode E13, a hole injection layer HIL13, a hole transport layer HTL13, a light-emitting layer LE13, an electron transport layer ETL13, and a second electrode E23 that are sequentially disposed on the substrate S13 in this order. The first electrode E13 may include a graphene layer. In this case, the graphene layer of the first electrode E13 may contact a top surface of the substrate S13. The light-emitting layer LE13 may include a QD-containing layer. For example, the light-emitting layer LE13 may be a QD layer. The structure of FIG. 9 may be substantially the same as that of FIG. 5, minus the plastic material layer P11.

A capping layer that is elastic may be further disposed on the optoelectronic device portion D13 of FIG. 9, as shown in FIG. 10.

Referring to FIG. 10, a stretchable device 100F may further include a capping layer C13 that is disposed on the optoelectronic device portion D13. The capping layer C13 may be substantially the same as the capping layer C10 of FIGS. 2 through 4. The optoelectronic device portion D13 may be located on or around an MNP. For example, the light-emitting layer LE13 of the optoelectronic device portion D13 may be located on or around the MNP. The structure of FIG. 10 may be substantially the same as that of FIG. 6, minus the plastic material layer P11.

According to example embodiments, an order in which constituent layers of the optoelectronic device portion D13 of FIGS. 9 and 10 are arranged may be vertically inverted. That is, an inverted structure obtained by vertically overturning the optoelectronic device portion D13 of FIGS. 9 and 10 may be applied to the substrate S13, as shown in FIGS. 11 and 12.

FIG. 11 is a cross-sectional view illustrating a stretchable optoelectronic device (hereinafter, referred to as a stretchable device) 100G according to example embodiments.

Referring to FIG. 11, an optoelectronic device portion D14 may be disposed on a substrate S14 that is elastic. The optoelectronic device portion D14 may have an inverted structure obtained by vertically overturning the optoelectronic device portion D13 of FIG. 9. That is, the optoelectronic device portion D14 may include a second electrode E24, an electron transport layer ETL14, a light-emitting layer LE14, a hole transport layer HIL14, a hole injection layer HIL14, and a first electrode E14 that are sequentially disposed on the substrate S14 in this order. In this case, the second electrode E24 may be referred to as a 'first electrode', and the first electrode E14 may be referred to as a 'second electrode'. The first electrode E14 may be an anode, and the second electrode E24 may be a cathode. The first electrode E14 may include a graphene layer, and the light-emitting layer LE14 may include a QD-containing layer.

The stretchable device 100G may further include an adhesive layer B14 that is disposed between the substrate S14 and the optoelectronic device portion D14. The adhesive layer B14 may be an organic adhesive layer. The adhesive layer B14 may be formed of a material that is substantially the same as that of the adhesive layer B12 of FIG. 7.

Also, the stretchable device 100G may further include a polymer layer PM14 that is disposed on the optoelectronic device portion D14. Accordingly, the optoelectronic device portion D14 may be disposed between the adhesive layer B14 and the polymer layer PM14. The polymer layer PM14 may include an elastomeric polymer. In this case, the polymer layer PM14 may be formed of a material that is substantially the same as an elastomeric polymer of the substrate S14. For example, the elastomeric polymer of the polymer layer PM14 may include at least one selected from the group consisting of silicon-based polymer, PU, PUA, acrylate polymer, and acrylate terpolymer. The silicon-based polymer may include at least one selected from the group consisting of, for example, PDMS, polyphenyl-methylsiloxane, and hexamethyldisiloxane. Also, ECOFLEX® (platinum-catalyzed silicones made by Smooth-On Inc.) may be used as the silicon-based polymer. However, the afore-described specific materials of the polymer layer PM14 are examples and other polymers may be used. The polymer layer PM14 may be disposed to contact the first electrode E14. When the first electrode E14 includes a graphene layer, the polymer layer PMN14 may contact the graphene layer. The polymer layer PM14 may have a relatively small thickness, for example, a thickness that is equal to or less than about 100 μm or about 50 μm.

A capping layer that is elastic may be further disposed on the polymer layer PM14 of FIG. 11, as shown in FIG. 12.

Referring to FIG. 12, a stretchable device 100H may further include a capping layer C14 that is disposed on the polymer layer PM14. The capping layer C14 may be substantially the same as the capping layer C10 of FIGS. 2 through 4. Since the capping layer C14 is provided, the optoelectronic device portion D14 may be located on or around an MNP. For example, the light-emitting layer LE14 of the optoelectronic device portion D14 may be located on or around the MNP.

FIG. 13 is a cross-sectional view illustrating a stretchable optoelectronic device (hereinafter, referred to as a stretchable device) 100K according to example embodiments. The example shown in FIG. 13 may be a modified example of the stretchable device 100B of FIG. 6.

Referring to FIG. 13, a plastic material layer P15 may be disposed on a substrate S15 that is elastic and a metal layer M15 may be disposed on a portion (for example, one end portion) of the plastic material layer P15. An optoelectronic device portion D15 may be disposed on the plastic material layer P15 and a portion of the metal layer M15, and thus, contact the portion of the metal layer M15. The optoelectronic device portion D15 may include a first electrode E15, a hole injection layer HIL15, a hole transport layer HTL15, a light-emitting layer LE15, an electron transport layer ETL15, and a second electrode E25 that are sequentially disposed on the substrate S15 in this order. The first electrode E15 may include a graphene layer, and the light-emitting layer LE15 may include a QD-containing layer. When the first electrode E15 includes a graphene layer, the graphene layer may contact the portion of the metal layer M15. A remaining portion of the metal layer M15 may not be covered by the graphene layer (of the first electrode E15) and may be exposed. The exposed remaining portion of the metal layer M15 may be a first contact portion CR1.

A capping layer C15 that is elastic may be disposed on the optoelectronic device portion D15. As the capping layer C15 is partially removed (etched), a portion of the second electrode E25 may be exposed. The exposed portion of the second electrode E25 may be a second contact portion CR2.

A desired (and/or alternatively predetermined) electrical signal may be input to the optoelectronic device portion D15 through the first contact portion CR1 and the second contact portion CR2. For example, a desired (and/or alternatively predetermined) voltage may be applied between the first electrode E15 and the second electrode E25 of the optoelectronic device portion D15 through the first contact portion UFO and the second contact portion CR2.

FIG. 13 illustrates a case where the stretchable device 100B of FIG. 6 includes the first and second contact portions CR1 and CR2. The first and second contact portions CR1 and CR2 may apply to the stretchable devices 100A and 100C through 100H of FIG. 5 and FIGS. 7 through 12. Also, structures/shapes/positions of the first and second contact portions CR1 and CR2 of FIG. 13 are examples and structures/units for electrically connecting the optoelectronic device portions D11 through D14 may be modified in various ways.

According to example embodiments, a plurality of device portions may be disposed on one substrate, as shown in FIG. 14.

Referring to FIG. 14, an optoelectronic device portion D100 having a wavy structure may be disposed on a substrate S100 that is elastic. A plastic material layer P100 may be disposed between the substrate S100 and the optoelectronic device portion D100 if necessary. The optoelectronic device portion D100 may include a graphene layer and a QD-containing layer. For example, the optoelectronic device portion D100 may include a first electrode E100, a hole injection layer HIL100, a hole transport layer HTL100, a light-emitting layer LE100, and an electron transport layer ETL100 that are sequentially disposed on the substrate S100 in this order. Also, the optoelectronic device portion D100 may include a plurality of second electrodes E201, E202, and E203 that are disposed on the electron transport layer ETL100. Portions of the optoelectronic device portions D100 respectively corresponding to the second electrodes E201, E202, and E203 may be 'unit device portions'. Accordingly, the optoelectronic device portion D100 may include a plurality of unit device portions. A capping layer C100 that is elastic may be further disposed on the optoelectronic device portion D100. Since the capping layer C100 is provided, the optoelectronic device portion D100 may be located on or around an MNP.

If necessary, at least a portion of a stack structure including the first electrode E100 to the electron transport layer ETL100 of FIG. 14 may be patterned into shapes similar to the second electrodes E201, E202, and E203. In other words, a plurality of optoelectronic device portions (that is, unit device portions) that are separate from one another may be disposed on one substrate and a capping layer that covers the plurality of optoelectronic device portions may be disposed on the substrate. A structure of HG. 14 may be modified in other various ways.

FIG. 15 is a cross-sectional view simplifying the structure of FIG. 14, according to example embodiments.

Referring to FIG. 15, an optoelectronic device portion D110 having a wavy structure may be disposed between a substrate S110 that is elastic and a capping layer C110 that is elastic. At least a portion of the optoelectronic device portion D110 may correspond to the optoelectronic device portions D10 through D100 of FIGS. 1 through 14. The substrate S110 and the capping layer C110 may respectively correspond to the substrates S10 through S100 and the capping layers C10 through C100 of FIGS. 1 through 14. Although not shown in FIG. 15, a plastic material layer, an adhesive layer (e.g., an organic adhesive layer), or a polymer layer may be further disposed between the substrate S110 and the optoelectronic device portion D110 and/or between the optoelectronic device portion D110 and the capping layer C110.

Each of the stretchable devices of FIGS. 5 through 15 may be a stretchable light-emitting device having a light-emitting surface that is stretchable and foldable. The light-emitting surface may be a surface of each of the light-emitting layers LE11 through LE15 and LE100. Since each of the light-emitting layers LE11 through LE15 and LE100 may include a QD-containing layer, the light-emitting surface may be a surface of the QD-containing layer. The feature that the light-emitting surface itself is stretchable or foldable may be necessary for a stretchable/foldable apparatus. For example, since the light-emitting surface is stretchable or foldable and characteristics of a portion of the light-emitting surface that is stretched or folded constant, various wearable electronic apparatuses and stretchable/foldable electronic apparatuses may be easily realized by using the light-emitting surface. Alternatively, each of the stretchable devices of FIGS. 5 through 15 may be a stretchable light-sensing device having a light-sensing surface that is stretchable and foldable. For example, a light-sensing layer may be substituted for the light-emitting layers LE11 through LE15 and LE100.

A QD-containing layer that may be included in each of the optoelectronic device portions D10 through D110 of FIGS. 1 through 15 may have, for example, such a structure as shown in FIG. 16. That is, FIG. 16 is a cross-sectional view illustrating a QD-containing layer that may be included in each of the stretchable devices of FIGS. 1 through 15, according to example embodiments.

Referring to FIG. 16, a QD-containing layer QDL1 may include a plurality of QDs. The plurality of QDs may have a single-layer or multi-layer structure. Each of the QDs may include a core portion c1 and a shell portion s1, and the shell portion s1 may have a single-shell or double-shell structure. The core portion c1 may include CdSe, InP, PbS, PbSe, or CdTe, and the shell portion s1 may include CdS or ZnS. The QD may have a diameter that is equal to or less than about 10 nm. For example, the QD may have a diameter that is a range from about 1 nm to about 10 nm. An organic ligand d1 may exist on a surface of the QD. The organic ligand d1 may be, for example, oleic acid, trioctylphosphine, trioctylamine, or trioctylphosphine oxide. The QD may be a colloidal QD.

In example embodiments, the quantum dots (QDs) may be formed of other suitable materials. For example, the quantum dots (QDs) may be graphene quantum dots (GQDs), silicon quantum dots, transition metal dichalcogenides (e.g., $MoS_2$, $MoSe_2$, $MoTe_2$, $WSe_2$, $WTe_2$, $WS_2$, $ZrS_2$, $ZrSe_2$, $HfS_2$, $HfSe_2$, and $NbSe_2$), and combinations thereof as the self-emissive materials for forming the light-emitting layer QDL1. One of ordinary skill in the art would appreciate that other light-emitting nano-materials may be used to form the quantum dots (QDs).

A method of manufacturing a stretchable optoelectronic device, according to example embodiments, will now be explained.

FIGS. 17A through 17F are cross-sectional views for explaining a method of manufacturing a stretchable optoelectronic device (hereinafter, referred to as a stretchable device), according to example embodiments.

Figure 17A:
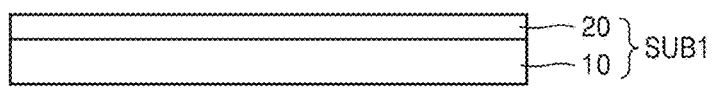

Referring to FIG. 17A, a first substrate SUB1 may be prepared. The first substrate SUB1 may include a rigid material 10 and a polymer layer 20. The right material 10 may be more rigid than the polymer layer 20. For example, the first substrate SUB1 may include a glass substrate 10 and the polymer layer 20. The glass substrate 10 may be the rigid material 10. The polymer layer 20 may be formed on the glass substrate 10. The polymer layer 20 may be referred to as a polymer substrate. The polymer layer 20 may include an elastomeric polymer. In this case, the polymer layer 20 may be formed of a material that is substantially the same as an elastomeric polymer of the substrate S10 of FIG. 1. For example, the elastomeric polymer of the polymer layer 20 may include at least one selected from the group consisting of silicon-based polymer, PU, PUA, acrylate polymer, and acrylate terpolymer. The silicon-based polymer may include at least one selected from the group consisting of, for example, PDMS, polyphenyl-methylsiloxane, and hexamethyldisiloxane. Also, ECOFLEX® (platinum-catalyzed silicones made by Smooth-On Inc.) may be used as the silicon-based polymer. However, the afore-described specific materials of the polymer layer 20 are examples and other various polymers may be used.

For example, when the polymer layer 20 is formed of PDMS, the polymer layer 20 may be formed by applying a mixture of a precursor (that is, a prepolymer) of the PDMS and a curing agent to the glass substrate 10 by using spin coating and then curing the mixture at a temperature of about 70° C. A weight ratio of the precursor to the curing agent in the mixture may be about 10:1, and the spin coating may be performed at a speed of about 6000 rpm. However, the afore-described detailed method of forming the polymer layer 20 is an example and various modifications may be made.

A thickness of the polymer layer 20 may be relatively small. For example, a thickness of the polymer layer 20 may be greater than 0 nm and equal to or less than about 100 μm or about 50 μm. When a thickness of the polymer layer 20 is small, problems that stress is applied to the polymer layer 20 or a volume of the polymer layer 20 is increased due to a subsequent heating process may be limited and/or prevented. To this end, the polymer layer 20 may be formed to have a relatively small thickness. The glass substrate 10, on which the polymer layer 20 is formed, may be formed of a rigid material and may function as a support substrate. That is, the glass substrate 10 may be used to improve handling of the stretchable device. The glass substrate 10 may be replaced by another substrate having a rigid material.

Figure 17B:
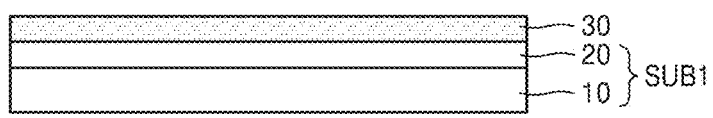

Referring to FIG. 17B, a plastic layer 30 may be formed on the first substrate SUB1. The plastic layer 30 may be attached to the polymer layer 20. The plastic layer 30 may be formed of a material that is substantially the same as that of each of the plastic material layers P10 and P11 of FIGS. 3 through 5. A Poisson's ratio of the plastic layer 30 may be less than 0.45 or 0.3. Also, the plastic layer 30 may have a Young's modulus that is greater than that of the polymer layer 20. For example, the plastic layer 30 may include at least one selected from the group consisting of PEN, PI, and PET. The plastic layer 30 may be easily attached to the polymer layer 20. A thickness of the plastic layer 30 may range from about 0.5 μm to about 100 μm or from about 0.5 μm to about 30 μm.

Figure 17C:
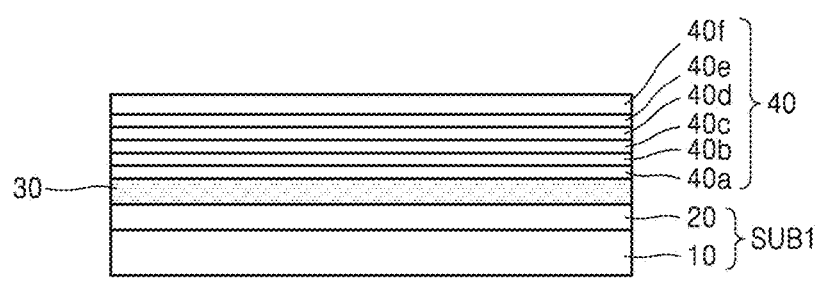

Referring to FIG. 17C, an optoelectronic device portion 40 may be formed on the plastic layer 30. The optoelectronic device portion 40 may be any one of a light-emitting device portion, a photovoltaic device portion, and a photo-detecting device portion (e.g., a light-sensing portion). The optoelectronic device portion 40 may include a graphene layer and a QD-containing layer. The optoelectronic device portion 40 may include a graphene layer and a layer formed of transition metal dichalcogenide (TMDC). When the optoelectronic device portion 40 is a light-emitting device portion, the optoelectronic device portion 40 may include a first electrode 40a, a light-emitting layer 40d, and a second electrode 40f that are sequentially disposed on the plastic layer 30 in this order. One of the first and second electrodes 40a and 40f may be an anode, and the other may be a cathode. For example, the first electrode 40a may be an anode, and the second electrode 40f may be a cathode. An anode from among the first and second electrodes 40a and 40f, for example, the first electrode 40a, may include a graphene layer. The graphene layer may have a single-layer structure including a single graphene layer or a multi-layer structure including graphene layers (e.g., less than about 100 or about 10 graphene layers). The light-emitting layer 40d that is disposed between the first and second electrodes 40a and 40f may include a QD-containing layer. For example, the light-emitting layer 40d may be a QD layer. The optoelectronic device portion 40 may further include a hole transport layer 40c that is disposed between the first electrode 40*a* and the light-emitting layer 40*d* and an electron transport layer 40*e* that is disposed between the second electrode 40*f* and the light-emitting layer 40*d*. Also, the optoelectronic device portion 40 may further include a hole injection layer 40*b* that is disposed between the first electrode 40*a* and the hole transport layer 40*c*. Materials of the first electrode 40*a*, the hole injection layer 40*b*, the hole transport layer 40*c*, the light-emitting layer 40*d*, the electron transport layer 40*e*, and the second electrode 40*f* may respectively correspond to those of the first electrode E11, the hole injection layer HIL11, the hole transport layer HTL11, the light-emitting layer LE11, the electron transport layer ETL11, and the second electrode E21 of FIG. 5. Although not shown in FIG. 17C, the optoelectronic device portion 40 may further include an electron injection layer (EIL) that is disposed between the second electrode 40*f* and the electron transport layer 40*e*.

When the first electrode 40*a* is formed of a graphene layer, the graphene layer may be transferred to the plastic layer 30. The graphene layer may be an undoped layer. If necessary, the graphene layer may be a layer doped with a p-type dopant. The hole injection layer 40*b* may be formed of PEDOT or PVK. For example, when the hole injection layer 40*b* is formed of PEDOT, the hole injection layer 40*b* may be formed by coating a mixed solution of PEDOT:dimethyl sulfoxide (DMSO):zonyl on the first electrode 40*a* to a thickness of tens of nanometers (nm) and thermally treating the mixed solution in a vacuum oven at a temperature of about 100° C. to about 250° C. by using annealing. Next, the hole transport layer 40*c*, the light-emitting layer 40*d*, and the electron transport layer 40*e* may be sequentially formed on the hole injection layer 40*b* by using a wet process. Next, the second electrode 40*f* may be formed on the electron transport layer 40*e*. The second electrode 40*f* may be formed of a metal or a metal compound such as an AL—Li alloy, Al, LiF/Al, Ag, Ca, Ca/Al, or Ca/Ag, or may be formed of doped graphene. Alternatively, the second electrode 40*f* may be formed of metal nanowires, CNTs, or graphene flakes. When the second electrode 40*f* is formed of an Al—Li alloy, for example, thermal evaporation may be used.

In addition, since the plastic layer 30 may have a high heat resistance when the optoelectronic device portion 40*c* is formed as described with reference to FIG. 17C, damage to the plastic layer 30 due to heat may be (limited and/or prevented). In particular, when the plastic layer 30 is formed of PEN, a high heat resistance may be ensured.

Figure 17D:
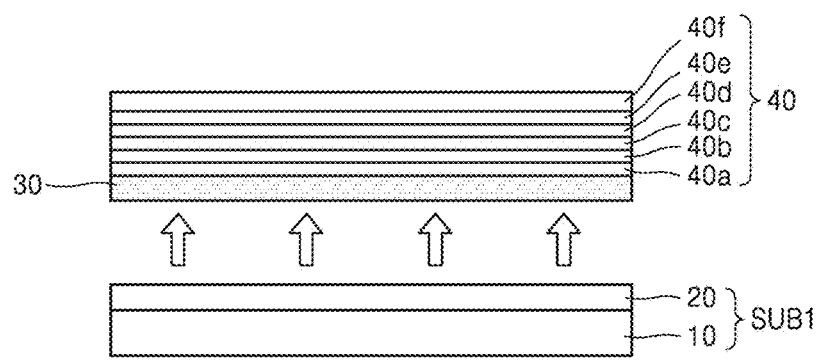

Referring to FIG. 17D, a stack structure including the plastic layer 30 and the optoelectronic device portion 40 may be separated from the first substrate SUB1. The stack structure including the plastic layer 30 and the optoelectronic device portion 40 may be separated from the first substrate SUB1 by physically separating the plastic layer 30 from the polymer layer 20. Since an adhesive force between the polymer layer 20 and the plastic layer 30 may be less than an adhesive force between the glass substrate 10 and the polymer layer 20 and an adhesive force between the plastic layer 3U and the optoelectronic device portion 40, the plastic layer 30 may be easily separated from the polymer layer 20. After the stack structure including the plastic layer 30 and the optoelectronic device portion 40 is separated from the first substrate SUB1, the plastic layer 30 may function as a support substrate or a handling substrate of the optoelectronic device portion 40.

Figure 17E:
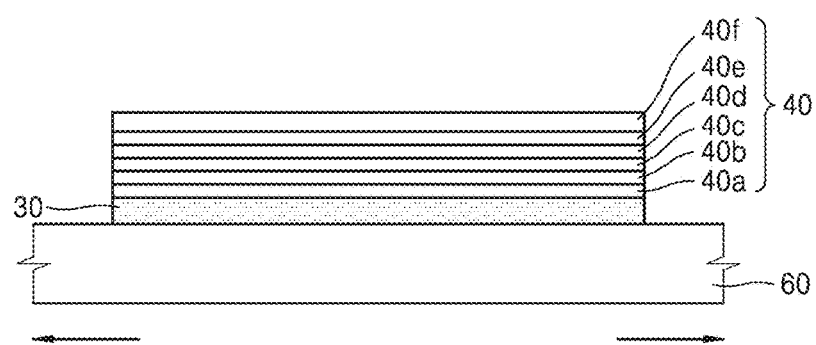

Referring to FIG. 17E, when a second substrate 60, including an elastomeric polymer is horizontally stretched, the stack structure including the plastic layer 30 and the optoelectronic device portion 40 may be attached to the second substrate 60. A material of the second substrate 60 may be substantially the same as that of the substrate S10 of FIG. 1. That is, the second substrate 60 may include the elastomeric polymer and may be stretchable. The elastomeric polymer may be elastomeric rubber. The elastomeric polymer of the second substrate 60 may be a material having a Poisson's ratio that is equal to or greater than 0.4 or 0.45. The elastomeric polymer of the second substrate 60 may include at least one selected from the group consisting of silicon-based polymer, PU, PUA, acrylate polymer, and acrylate terpolymer. The silicon-based polymer may include at least one selected from the group consisting of, for example, PDMS, polyphenyl-methylsiloxane, and hexamethyldisiloxane. Also, ECOFLEX® (platinum-catalyzed silicones made by Smooth-On Inc.) may be used as the silicon-based polymer. However, the afore-described specific materials of the second substrate 60 are an example and other various elastomeric polymers may be used. When the second substrate 60 is horizontally stretched by a desired (and/or alternatively predetermined) length, the stack structure including the plastic layer 30 and the optoelectronic device portion 40 may be attached to the second substrate 60. In this case, the plastic layer 30 may be easily attached to the second substrate 60. If necessary, a desired (and/or alternatively predetermined) adhesive (e.g., an adhesive layer) may be further disposed between the plastic layer 30 and the second substrate 60.

In FIG. 17E, a degree to which the second substrate 60 is horizontally stretched, that is, prestrain of the second substrate 60, may be equal to or greater than about 5% or about 10%. Prestrain of the second substrate 60 may be equal to or greater than about 50% or about 100%. The optoelectronic device portion 40 may be formed on the prestrained second substrate 60.

Figure 17F:
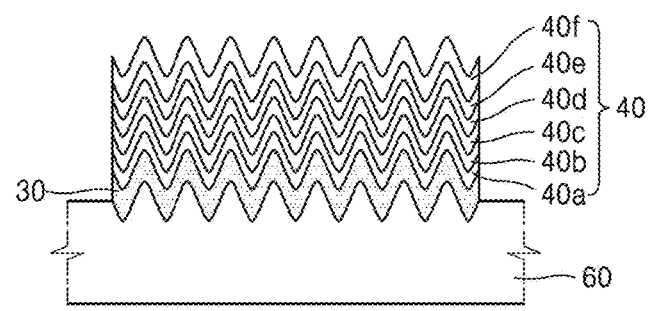

Next, when tensile strain applied to the second substrate 60 is removed, as shown in FIG. 17F, a wavy structure may be formed in the optoelectronic device portion 40. The optoelectronic device portion 40 having the wavy structure may be horizontally stretchable along with the second substrate 60 and may be foldable at a wide angle. In this case, the plastic layer 30 may be disposed between the second substrate 60 and the optoelectronic device portion 40. The wavy structure of the optoelectronic device portion 40 may have a desired (and/or alternatively predetermined) wavelength and a desired (and/or alternatively predetermined) amplitude. An average wavelength of the wavy structure of the optoelectronic device portion 40 may range from about 3 μm to about 3 mm or from about 10 μm to about 2 mm, and an average amplitude of the wavy structure of the optoelectronic device portion 40 may range from about 50 nm to about 2 mm or from about 100 nm to about 1 mm. A wavelength (e.g., an average wavelength) and an amplitude (e.g., an average amplitude) of the wavy structure the optoelectronic device portion 40 may be adjusted according to a thickness of the plastic layer 30. The stretchable device of FIG. 17F may correspond to the stretchable device 100A of FIG. 5.

According to example embodiments, a capping layer including an elastomeric polymer may be further formed on the optoelectronic device portion 40 of FIG. 17E or 17F, as shown in FIG. 18.

Referring to FIG. 18, a capping layer 70 including an elastomeric polymer may be formed on the optoelectronic device portion 40. The capping layer 70 may be formed in a step of FIG. 17E or a step of FIG. 17F. The optoelectronic device portion 40 may be disposed between the second substrate 60 and the capping layer 70. In this case, the optoelectronic device portion 40 may be located on or around an MNP. The light-emitting layer 40d of the optoelectronic device portion 40 may be located on or around the MNP. The capping layer 70 may be formed of a material that is substantially the same as that of the capping layer C10 of FIG. 2. For example, the elastomeric polymer of the capping layer 70 may include at least one selected from the group consisting of PU, PUA, acrylate polymer, acrylate terpolymer, and silicon-based polymer. The silicon-based polymer may include at least one selected from the group consisting of, for example, PDMS, polyphenyl-methylsiloxane, and hexamethyldisiloxane. Also, ECOFLEX® (platinum-catalyzed silicones made by Smooth-On Inc.) may be used as the silicon-based polymer. However, the afore-described specific materials of the capping layer 70 are an example and other elastomeric polymers may be used. The stretchable device of FIG. 18 may correspond to the stretchable device 100B of FIG. 6.

FIGS. 19A through 19D are cross-sectional views for explaining a method of manufacturing a stretchable optoelectronic device portion (hereinafter, referred to as a stretchable device), according to example embodiments.

Figure 19A:
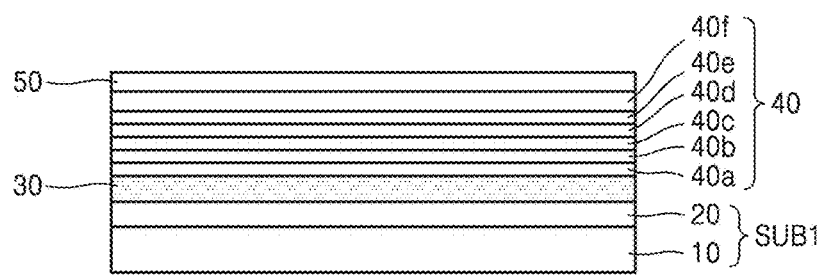

Referring to FIG. 19A, the plastic layer 30 and the optoelectronic device portion 40 may be formed on the first substrate SUB1 by using the method of FIGS. 17A through 17C. Next, an adhesive layer 50 may be further formed on the optoelectronic device portion 40. The adhesive layer 50 may be an organic adhesive layer. The adhesive layer 50 may be formed of a material that is substantially the same as that of the capping layer 70 of FIG. 18. For example, the adhesive layer 50 may include at least one selected from the group consisting of PU, PUA, acrylate polymer, acrylate terpolymer, and silicon-based polymer. The silicon-based polymer may include at least one selected from the group consisting of, for example, PDMS, polyphenyl-methylsiloxane, and hexamethyldisiloxane.

Figure 19B:
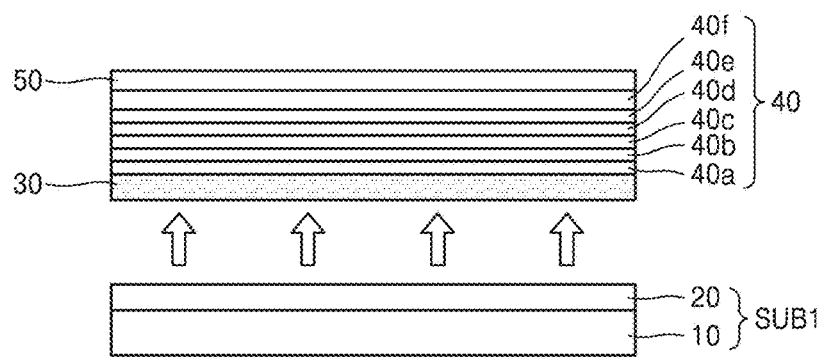

Referring to FIG. 19B, a stack structure including the plastic layer 30, the optoelectronic device portion 40, and the adhesive layer 50 may be separated from the first substrate SUB1, like described with reference to FIG. 17D.

Figure 19C:
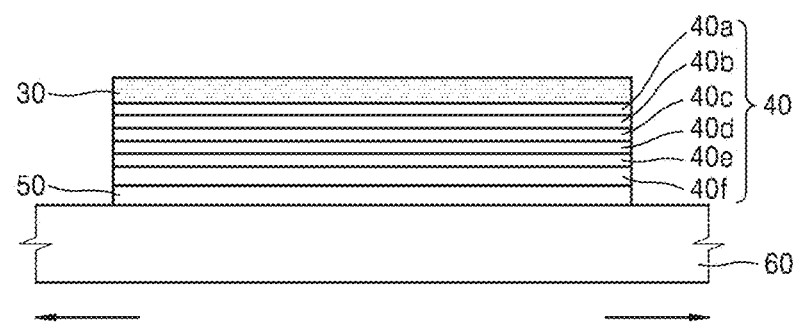

Referring to FIG. 19C, when the second substrate 60, including an elastomeric polymer, is horizontally stretched, the stack structure including the plastic player 30, the optoelectronic device portion 40, and the adhesive layer 50 may be attached to the second substrate 60. In this case, the adhesive layer 50 may be attached to a surface of the second substrate 60. Accordingly, the optoelectronic device portion 40 that is vertically overturned may be disposed on the second substrate 60. The optoelectronic device portion 40 may include the second electrode 40f, the electron transport layer 40e, the light-emitting layer 40d, the hole transport layer 40c, the hole injection layer 40b, and the first electrode 40a that are sequentially disposed on the second substrate 60 in this order. The first electrode 40a may be an anode, and the second electrode 40f may be a cathode. The first electrode 40a may include a graphene layer, and the light-emitting layer 40d may include a QD-containing layer.

Figure 19D:
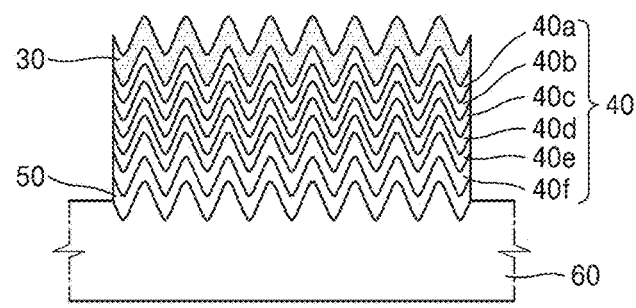

Next, when tensile strain applied to the second substrate 60 is removed, as shown in FIG. 19D, a wavy structure may be formed in the optoelectronic device portion 40. The stretchable device of FIG. 19D may correspond to the stretchable device 100C of FIG. 7.

According to example embodiments, a capping layer including an elastomeric polymer may be further formed on the plastic layer 30 of FIG. 19C or 19D, as shown in FIG. 20.

Referring to FIG. 20, the capping layer 70 including an elastomeric polymer may be formed on the plastic layer 30. The capping layer 70 may be formed in a step of FIG. 19C or a step of FIG. 19D. The plastic layer 30 may be disposed between the optoelectronic device portion 40 and the capping layer 70, and the optoelectronic device portion 40 may be disposed between the second substrate 60 and the capping layer 70. The optoelectronic device portion 40 may be located on or around an MNP. The capping layer 70 may be formed of a material that is substantially the same as that of the capping layer 70 of FIG. 18. The stretchable device of FIG. 20 may correspond to the stretchable device 100D of FIG. 8.

According to example embodiments, when a substrate, including an elastomeric polymer, is horizontally stretched, an optoelectronic device portion including a graphene layer and a QD-containing layer may be formed on the stretched substrate, and then tensile strain applied to the substrate may be removed and a wavy structure in the optoelectronic device portion is formed, as shown in FIGS. 21A through 21C.

FIGS. 21A through 21C are cross-sectional views for explaining a method of manufacturing a stretchable optoelectronic device (hereinafter, referred to as a stretchable device), according to example embodiments.

Referring to FIG. 21A, a substrate 62 including an elastomeric polymer may be horizontally stretched. Examples of a method of stretching the substrate 62 may include a physical stretching method and a thermal stretching method. In the physical stretching method, at least both ends of the substrate 62 may be pulled out to stretch the substrate 62. In the thermal stretching method, the substrate 62 may be stretched in all directions. One of the physical stretching method and the thermal stretching method may be used or both the physical stretching method and the thermal stretching method may be used.

Referring to FIG. 21B, an optoelectronic device portion 42 may be formed on the stretched substrate 62. The optoelectronic device portion 42 may include, for example, a first electrode 42a, a hole injection layer 42b, a hole transport layer 42c, a light-emitting layer 42d, an electron transport layer 42e, and a second electrode 42f that are sequentially disposed on the substrate 62 in this order. The first electrode 42a may include a graphene layer. In this case, the graphene layer of the first electrode 42a may contact a top surface of the substrate 62. The light-emitting layer 42d may include a QD-containing layer. For example, the light-emitting layer 42d may be a QD layer. A method of forming the first electrode 42a, the hole injection layer 42b, the hole transport layer 42c, the light-emitting layer 42d, the electron transport layer 42e, and the second electrode 42f may be substantially the same as that used to form the first electrode 40a, the hole injection layer 40b, the hole transport layer 40c, the light-emitting layer 40d, the electron transport layer 40e, and the second electrode 40f of FIG. 17C, respectively.

Referring to FIG. 21C, a wavy structure of the optoelectronic device portion 42 may be formed by removing tensile strain applied to the substrate 62. The stretchable device of FIG. 21C may correspond to the stretchable device 100E of FIG. 9.

According to example embodiments, a capping layer including an elastomeric polymer may be further formed on the optoelectronic device portion 42 of FIG. 21B or 21C, as shown in FIG. 22.

Referring to FIG. 22, a capping layer 72 including an elastomeric polymer may be formed on the optoelectronic device portion 42. The capping layer 72 may be formed in a step of FIG. 21B or a step of FIG. 21C. The optoelectronic device portion 42 may be disposed between the second substrate 62 and the capping layer 72. The optoelectronic device portion 42 may be located on or around an MNP. The capping layer 72 may be formed of a material that is substantially the same as that of the capping layer 70 of FIG. 18. The stretchable device of FIG. 22 may correspond to the stretchable device 100F of FIG. 10.

FIGS. 23A through 23D are cross-sectional views for explaining a method of manufacturing a stretchable optoelectronic device (hereinafter, referred to as a stretchable device), according to example embodiments.

Figure 23A:
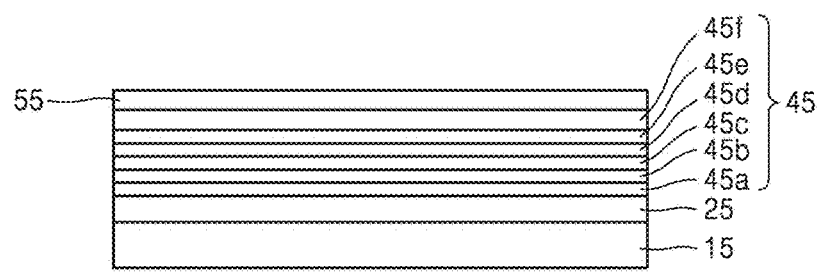

Referring to FIG. 23A, a polymer layer 25 may be formed on a glass substrate 15, and an optoelectronic device portion 45 may be formed on the polymer layer 25 by using a method that is similar to the method of FIGS. 17A through 17C. In this case, the polymer layer 25 may have a thickness that ranges from, for example, about 500 µm to about 2 mm. The optoelectronic device portion 45 may include a first electrode 45a, a hole injection layer 45b, a hole transport layer 45c, a light-emitting layer 45d, an electron transport layer 45d, and a second electrode 45f that are sequentially stacked on the polymer layer 25 in this order. Next, an adhesive layer 55 may be formed on the optoelectronic device portion 45. The adhesive layer 55 may be substantially the same as the adhesive layer 50 of FIG. 19A.

Figure 23B:
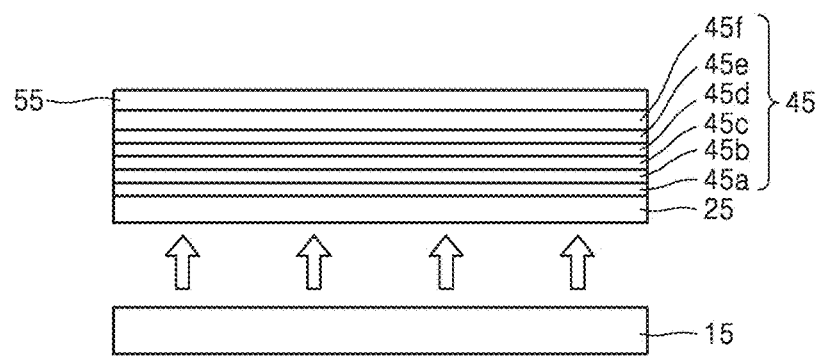

Referring to FIG. 23B, a stack structure including the polymer layer 25, the optoelectronic device portion 45, and the adhesive layer 55 may be separated from the glass substrate 15. The stack structure may be separated from the glass substrate 15 by physically separating the polymer layer 25 from the glass substrate 15. Since an adhesive force between the glass substrate 15 and the polymer layer 25 is less than an adhesive force between the polymer layer 25 and the optoelectronic device portion 45, the polymer layer 25 may be easily separated from the glass substrate 15. In this case, the polymer layer 25 may support the optoelectronic device portion 45 and (limit and/or prevent) the optoelectronic device portion 45 from being damaged or cracked. To this end, a thickness of the polymer layer 25 may be relatively large. For example, a thickness of the polymer layer 25 may range from about 500 µm to about 2 mm.

Figure 23C:
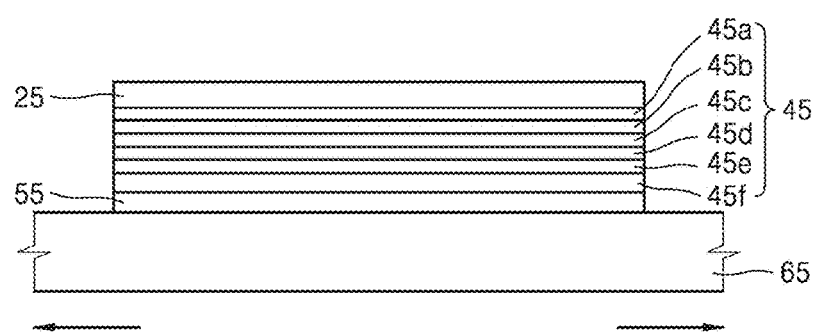

Referring to FIG. 23C, when the second substrate 65, including an elastomeric polymer, is horizontally stretched, the stack structure including the polymer layer 25, the optoelectronic device portion 45, and the adhesive layer 55 may be attached to the stretched second substrate 65. In this case, the adhesive layer 55 may be attached to the second substrate 65. Accordingly, the optoelectronic device portion 45 that is vertically overturned may be disposed on the second substrate 65. That is, the optoelectronic device portion 45 may include the second electrode 45f, the electron transport layer 45d, the light-emitting layer 45d, the hole transport layer 45c, the hole injection layer 45b, and the first electrode 45a that are sequentially disposed on the second substrate 65 in this order. The polymer layer 25 may be disposed on the optoelectronic device portion 45.

Figure 23D:
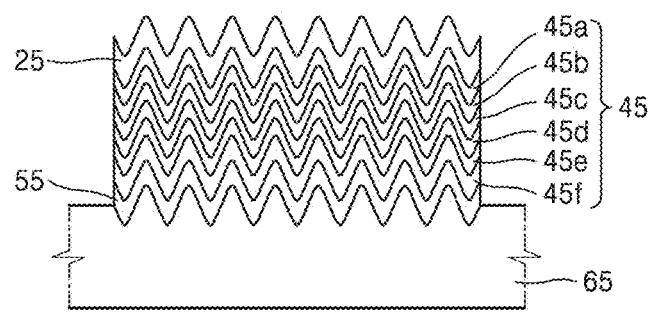

Referring to FIG. 23D, a wavy structure may be formed in the optoelectronic device portion 45 by removing tensile strain applied to the second substrate 65. The stretchable device of FIG. 23D may correspond to the stretchable device 100G of FIG. 11.

According to example embodiments, a capping layer including an elastomeric polymer may be further formed on the polymer layer 25 of FIG. 23C or 23D, as shown in FIG. 24.

Referring to FIG. 24, a capping layer 75 including an elastomeric polymer may be formed on the polymer layer 25. The capping layer 75 may be formed in a step of FIG. 23C or a step of FIG. 23D. The polymer layer 25 may be disposed between the optoelectronic device portion 45 and the capping layer 75, and the optoelectronic device portion 45 may be disposed between the second substrate 65 and the capping layer 75. The optoelectronic device portion 45 may be located on or around an MNP. The capping layer 75 may be formed of a material that is substantially the same as that of the capping layer 70 of FIG. 18. The stretchable device of FIG. 24 may correspond to the stretchable device 100H of FIG. 12.

FIG. 25 is a plan image illustrating a wavy structure of a graphene/PEDOT stack structure that may be applied to a stretchable/foldable optoelectronic device, according to example embodiments. The graphene/PEDOT stack structure was formed on a prestrained PDMS substrate and then, when tensile strain applied to the PDMS substrate was removed, had a wavy structure. In this case, prestrain of the PDMS substrate was 25%. The plan image of FIG. 25 was captured by using an optical microscope.

Referring to FIG. 25, a wavy structure is formed in the graphene/PEDOT stack structure and the wavy structure has a relatively uniform waveform.

FIG. 26 is a graph illustrating a relationship between a thickness of a PEDOT layer of a graphene/PEDOT stack structure and a wavelength of a wavy structure, according to example embodiments. The graphene/PEDOT stack structure was formed on a prestrained PDMS substrate and then, when tensile strain applied to the PDMS substrate was removed, had a wavy structure. In this case, prestrain of the PDMS substrate was 25%. Also, FIG. 26 illustrates a relationship between a thickness of the PEDOT layer and a wavelength of the wavy structure when only the PEDOT layer without graphene is formed on the PDMS substrate.

Referring to FIG. 26, both when the graphene/PEDOT stack structure is used and when only the PEDOT layer without graphene is used, a wavelength (e.g., an average wavelength) of the wavy structure increases as a thickness of the PEDOT layer increases. Also, a wavelength (e.g., an average wavelength) of the wavy structure when both the PEDOT layer and the graphene are used is slightly higher than that when only the PEDOT layer is used. It seems because when both the PEDOT layer and the graphene are used, a Young's modulus of the wavy structure is increased due to the graphene.

FIGS. 27A through 27F are plan images illustrating a morphology while a graphene/PEDOT stack structure is stretched, according to example embodiments. A graphene/PEDOT stack structure was formed on a PDMS substrate that was prestrained to 25% and then, a graphene/PEDOT structure having a wavy structure was formed by removing a tensile stress applied to the PDMS substrate. A morphology was measured while the graphene/PEDOT structure was stretched. Tensile strain was 0% in FIG. 27A, tensile strain was 5% in FIG. 27B, tensile strain was 10% in FIG. 27C, tensile strain was 15% in FIG. 27D, tensile strain was 20% in FIG. 27E, and tensile strain was 25% in FIG. 27F.

Figure 27A:
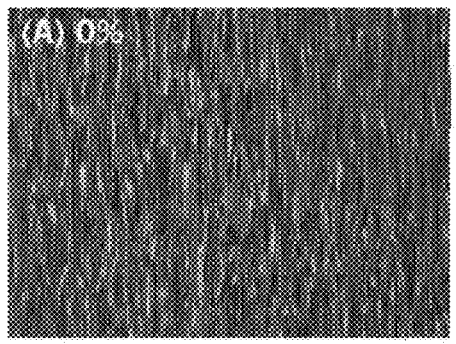
Figure 27B:
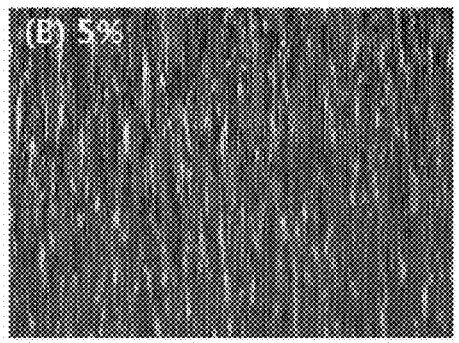
Figure 27C:
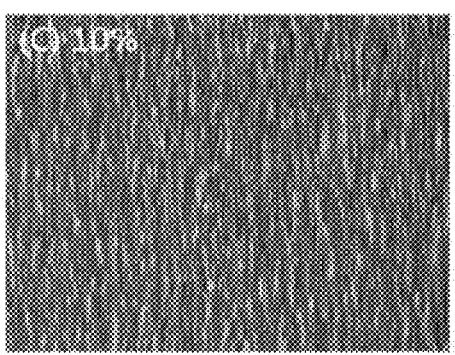
Figure 27D:
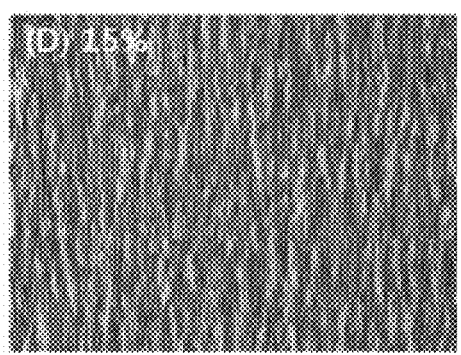
Figure 27E:
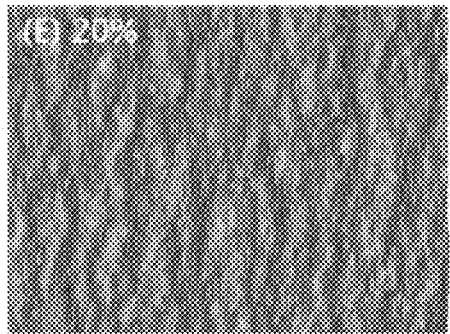
Figure 27F:
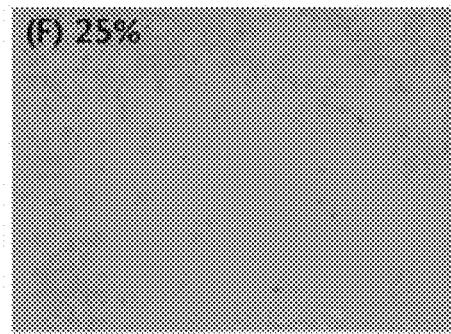

Referring to FIGS. 27A through 27F, as tensile strain increases, that is, as the stretching changes from FIG. 27A to FIG. 27F, the number of waves gradually decreases. In FIG. 27F, that is, when tensile strain is about 25%, there is little corrugation on a surface of the graphene/PEDOT stack structure. Such a result is related to prestrain of the PDMS substrate. As prestrain of the PDMS substrate increases, tensile strain of the graphene/PEDOT structure may increase.

FIG. 28 is a graph illustrating a relationship between strain of a graphene/PEDOT stack structure having a wavy structure and a sheet resistance (Ω/sq), according to example embodiments. The graphene/PEDOT stack structure was formed on a PDMS substrate that was prestrained to 30% and in this case, a thickness of a PEDOT layer was 55 nm.

Referring to FIG. 28, until strain (e.g., tensile strain) is about 30%, sheet resistance is barely changed. When strain increases to be equal to or greater than 30%, sheet resistance slightly increases. When strain is 50%, sheet resistance is about 127 Ω/sq, which may be low enough for the graphene/PEDOT stack structure to be used as an anode. It is found from FIG. 28 that a sheet resistance is barely changed until strain is the same as or equal to prestrain of the PDMS substrate and is not greatly increased even after strain is greater than the prestrain of the PDMS substrate.

FIG. 29 is a graph illustrating a result obtained after measuring a transmittance of a PDMS/graphene/PEDOT stack structure having a wavy structure, according to example embodiments. A transmittance of the PDMS/graphene/PEDOT stack structure was measured by changing a wavelength of light from about 275 nm to about 800 nm. In the PDMS/graphene/PEDOT stack structure, a thickness of a PEDOT layer was 50 nm and a graphene layer was a single graphene sheet. Also, FIG. 29 shows transmittance data of a PDMS substrate having a thickness of 2.4 mm.

Referring to FIG. 29, a transmittance of the PDMS substrate itself is equal to or greater than 90%, which is very high. Also, a transmittance of the PDMS/graphene/PEDOT stack structure ranges from about 80% to about 90%, which is also high. When a wavelength of light is 550 nm, a transmittance of the PDMS/graphene/PEDOT stack structure is about 87.2%. Accordingly, the PDMS/graphene/PEDOT stack structure may be transparent or almost transparent. Accordingly, the PDMS/graphene/PEDOT structure may be effectively applied to an optical device (e.g., a light-emitting device).

A sheet resistance of a graphene/PEDOT stack structure of FIG. 29 was about 92 Ω/sq. A resistance of the graphene/PEDOT stack structure may be about 4 to 7 times less than a resistance of one graphene or the PEDOT layer having the same thickness as that of one graphene layer. Accordingly, the graphene/PEDOT stack structure may be used as an anode.

FIGS. 30A through 30D are plan images illustrating a wavy structure of a QD layer that is transfer-printed onto a prestrained PDMS substrate, according to example embodiments. A thickness of the QD layer was 40 nm in FIG. 30A, a thickness of the QD layer is 90 nm in FIG. 30B, a thickness of the QD layer is 120 nm in FIG. 30C, and a thickness of the QD layer is 200 nm in FIG. 30D.

Referring to FIGS. 30A through 30D, as a thickness of the QD layer increases, that is, as the stretching changes from FIG. 30A to FIG. 30D, a wavelength of the wavy structure increases. An average wavelength of the wavy structure was about 4.85 μm in FIG. 30A, an average wavelength of the wavy structure was about 10.95 μm in FIG. 30B, an average wavelength of the wavy structure was about 14.9 μm in FIG. 30C, and an average wavelength of the wavy structure was about 20 μm in FIG. 30D. A Young's modulus of the QD layer that was calculated from an equation by using the measured average wavelengths of the wavy structure of FIGS. 30A through 30D was about 47 GPa.

FIG. 31 is a graph illustrating a relationship between a thickness of a QD layer that is transfer-printed onto a prestrained PDMS substrate and a wavelength of a wavy structure, according to example embodiments.

Referring to FIG. 31, as a thickness of the QD layer increases, a wavelength (e.g., an average wavelength) of the wavy structure increases, which corresponds to a result of FIGS. 30A through 30D.

FIGS. 32A through 32D are plan images illustrating a morphology while stretching a PEN/graphene stack structure that is formed on an elastic substrate (e.g., an ECOFLEX® substrate), according to example embodiments. ECOFLEX® is a platinum-catalyzed silicones made by Smooth-On Inc. The PEN/graphene stack structure was formed on the ECOFLEX® substrate (ECOFLEX® is a platinum-catalyzed silicones made by Smooth-On Inc.) that was prestrained to 70%, and then, a PEN/graphene structure having a wavy structure was formed by removing tensile strain applied to the ECOFLEX® substrate (ECOFLEX® is a platinum-catalyzed silicones made by Smooth-On Inc.). A morphology was measured while the PEN/graphene structure was stretched. A thickness of a PEN layer was 1.3 μm. Tensile strain was 0% in FIG. 32A, tensile strain was 30% in FIG. 32B, tensile strain was 50% in FIG. 32C, and tensile strain was 70% in FIG. 32D.

Figure 32A:
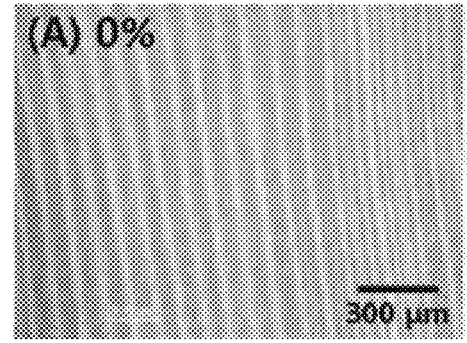
Figure 32B:
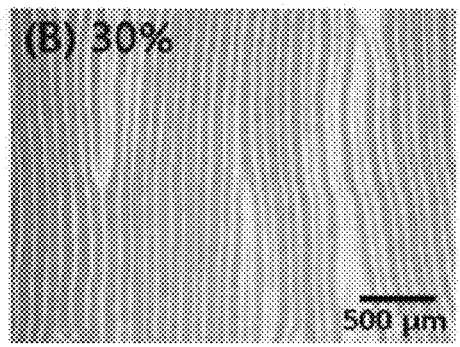
Figure 32C:
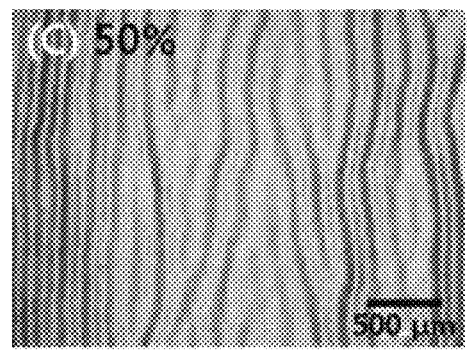
Figure 32D:
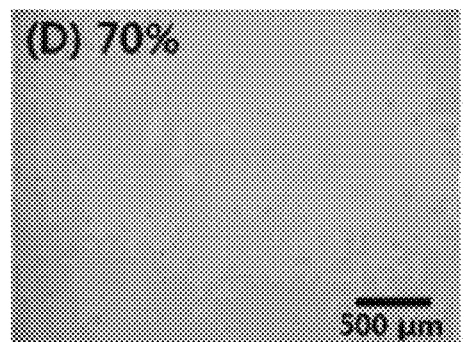

Referring to FIGS. 32A through 32D, as tensile strain increases, that is, as the drawing changes from FIG. 32A to FIG. 32D, the number of waves gradually decreases. In FIG. 32D, that is, when tensile strain is 70%, there is little corrugation on a surface of the PEN/graphene stack structure. Such a result is related to prestrain of the Ecoflex substrate. As prestrain of the Ecoflex substrate increases, tensile strain of the PEN/graphene stack structure may increase.

FIGS. 33A and 33B are plan images illustrating a uniaxial wavy structure and a multiaxial wavy structure of an optoelectronic device, according to example embodiments. The multiaxial wavy structure of FIG. 33B is a biaxial wavy structure. A substrate that is elastic may be stretched in one direction (e.g., in an X-axis direction) or in both directions (e.g., X and Y-axes directions) and then an optoelectronic device portion having a multi-layer structure may be formed on the stretched substrate, and an optoelectronic device having the uniaxial wavy structure (see FIG. 33A) or the multiaxial wavy structure (see FIG. 33B) may be obtained by removing tensile strain applied to the substrate. As shown in FIGS. 33A and 33B, a wavy structure that may be stretched in one axis direction or in multi-axis directions without cracks may be manufactured.

FIGS. 34A and 34B are images illustrating an operation of a stretchable/foldable optoelectronic device (e.g., a light-emitting device), according to example embodiments. FIG. 34A illustrates a green light-emitting device and FIG. 34B illustrates a red light-emitting device. The optoelectronic device of example embodiments was formed by attaching an optoelectronic device portion including a graphene layer and a QD layer to a prestrained PDMS substrate. A PEN layer was disposed between the PDMS substrate and the optoelectronic device portion.

FIG. 35 is an image illustrating a case where the optoelectronic device of FIGS. 34A and 34B is bent and folded, according to example embodiments. Referring to FIG. 35, even when the optoelectronic device according to example embodiments is bent or folded, the optoelectronic device may normally operate without any deterioration in electrical and optical characteristics. In this case, a bending radius of the optoelectronic device may be equal to or less than 1 mm.

FIGS. 36A through 36C are images illustrating a case where a stretchable/foldable optoelectronic device (e.g., a light-emitting device) is stretched, according to example embodiments. The optoelectronic device of example embodiments was formed by attaching an optoelectronic device portion including a graphene layer and a QD layer to a prestrained PDMS substrate. A PEN layer was disposed between the PDMS substrate and the optoelectronic device portion. A thickness of the PEN layer was 12 μm. It is found from FIGS. 36A through 36C that even when an optoelectronic device (e.g., a light-emitting device) is tensile-deformed by about 23%, light emitting characteristics thereof are maintained.

FIG. 37 is a graph illustrating an electroluminescence (EL) spectrum of a stretchable/foldable optoelectronic device (e.g., a light-emitting device), according to example embodiments. In FIG. 37, a curve A corresponds to a green light-emitting device and a curve B corresponds to a red light-emitting device. A method of manufacturing the optoelectronic device was the same as that of FIG. 36.

Referring to FIG. 37, each of the curve A and the curve B has a high intensity and little noise at a wavelength of a color corresponding thereto. A full width at half maximum (FWHM) of each device was less than just 30 nm due to optical properties of QDs, which means that each device has high color purity.

FIG. 38 is a graph illustrating voltage-current density characteristics of a stretchable/foldable optoelectronic device (e.g., a light-emitting device), according to example embodiments. In FIG. 38, a curve A corresponds to a green light-emitting device and a curve B corresponds to a red light-emitting device. In FIG. 38, a voltage refers to a voltage that is applied between two electrodes (e.g., first and second electrodes) of the optoelectronic device and a current density refers to a current density between the two electrodes.

FIG. 39 is a graph illustrating voltage-brightness characteristics of a stretchable/foldable optoelectronic device (e.g., a light-emitting device), according to example embodiments. In FIG. 39, a curve A corresponds to a green light-emitting device and a curve B corresponds to a red light-emitting device. Referring to FIG. 39, a maximum brightness of the stretchable/foldable optoelectronic device was as much as about 1200 cd/m$^2$.

FIG. 40 is a graph illustrating current density-luminous efficiency characteristics of a stretchable/foldable optoelectronic device (e.g., a light-emitting device), according to example embodiments. In FIG. 40, a curve A corresponds to a green light-emitting device and a curve B corresponds to a red light-emitting device. Referring to FIG. 40, a maximum efficiency of the stretchable/foldable optoelectronic device was as much as about 1 cd/A.

FIG. 41 is an image illustrating an optoelectronic device (e.g., a light-emitting device) that is directly formed on a prestrained PDMS substrate without using a plastic material layer such as a PEN layer, according to example embodiments. The optoelectronic device was a light-emitting device using graphene-QDs.

FIGS. 42 and 43 are graphs illustrating a result obtained after evaluating characteristics of the optoelectronic device of FIG. 41, according to example embodiments. FIG. 42 illustrates voltage-current density characteristics of the optoelectronic device and FIG. 43 illustrates voltage-brightness characteristics of the optoelectronic device.

FIG. 44 is an image illustrating an optoelectronic device (e.g., a light-emitting device) that is manufactured by using a plastic material layer (e.g., a PEN layer) on a prestrained PDMS substrate, according to example embodiments. The optoelectronic device was a light-emitting device using graphene-QDs. In this case, a thickness of the plastic material was 25 μm.

FIGS. 45A through 45C are images illustrating a case where the optoelectronic device of FIG. 44 is stretched, according to example embodiments. FIG. 46 is an image illustrating a case where the optoelectronic device (light-emitting device) of FIG. 44 is bent, according to example embodiments. It is found from FIGS. 45A through 45C that tensile strain of the optoelectronic device is equal to or greater than about 8% and it is found from FIG. 46 that a bending radius of the optoelectronic device is equal to or less than about 1 mm.

FIGS. 47 through 49 are graphs illustrating results obtained after evaluating characteristics of a stretchable/foldable optoelectronic device (e.g., a light-emitting device), according to example embodiments. FIG. 47 illustrates voltage-current density characteristics of the stretchable/foldable optoelectronic device, FIG. 48 illustrates voltage-brightness characteristics of the stretchable/foldable optoelectronic device, and FIG. 49 illustrates current density-luminous efficiency characteristics the stretchable/foldable optoelectronic device. The optoelectronic device of example embodiments was formed by attaching an optoelectronic device portion including a graphene layer and a QD layer to a prestrained elastic substrate. A PEN layer was disposed between the elastic substrate and the optoelectronic device portion. In this case, a thickness of the PEN layer was about 12 μm. The optoelectronic device was a red light-emitting device. A maximum brightness in FIG. 48 was equal to or greater than as much as 1200 cd/m$^2$ and a maximum luminous efficiency in FIG. 49 was as much as about 2.3 cd/A.

FIG. 50 is a graph illustrating current density-luminous efficiency characteristics of a light-emitting device, according to a comparative example. The light-emitting device according to the comparative example was a rigid light-emitting device including a QD layer and using an indium tin oxide (ITO) electrode. Referring to FIG. 50, a maximum luminous efficiency of the light-emitting device according to the comparative example is just about 0.43 cd/A. When compared with a maximum luminous efficiency of about 2.3 cd/A of the light-emitting device according to example embodiments of FIG. 49, the maximum efficiency of about 0.43 cd/A is much low.

FIG. 51 is a graph illustrating a result obtained after measuring a heart rate of a subject (e.g., a person) by using a photoplethysmograhy (PPG) sensor using a stretchable/foldable optoelectronic device (e.g., a light-emitting device) according to example embodiments. The PPG sensor may be fit around the subject's finger, and the stretchable/foldable optoelectronic device according to example embodiments may be used as a light source of the PPG sensor. In this case, the light source may be required to be wearable/stretchable. The PPG sensor may be used to measure a heart rate by detecting a change in a transmittance of light due to blood flow in a body part such as the finger.

Referring to FIG. 51, PPG signal pulses are repeatedly and clearly shown. Accordingly, it is determined that the stretchable/foldable optoelectronic device normally operates in the PPG sensor.

FIG. 52 is a graph illustrating a pulse corresponding to one cycle among PPG signal pulses that are measured by using a PPG sensor using a stretchable/foldable optoelectronic device (e.g., a light-emitting device), according to example embodiments.

FIG. 53 is a graph illustrating a pulse corresponding to one cycle among PPG signal pulses that are measured by using a PPG sensor using a light-emitting device, according to a comparative example. The light-emitting device according to the comparative example may be the same as the light-emitting device according to the comparative example of FIG. 50.

The graphs of FIGS. 52 and 53 will be compared with each other. When the light-emitting device according to the comparative example (see FIG. 53) is used, noise is much higher and a signal state is much worse than that when the stretchable/foldable optoelectronic device according to example embodiments (see FIG. 52) is used. Accordingly, when the stretchable/foldable optoelectronic device according to example embodiments is used, excellent characteristics may be obtained.

FIG. 54 is a system diagram of a sensor system according to example embodiments.

Referring to FIG. 54, a sensor system may be realized using a mobile equipment device and an electronic patch. The mobile equipment device may include a controller, a communication chip (e.g., radio chipset), a drive integrated circuit (IC), and an application processor. The application processor may include a central processing unit (CPU), a random access memory (RAM), and a memory chip. The electronic patch may include an antenna, a communication chip (e.g., radio chipset), a supercapacitor, and an optoelectronic sensor. The optoelectronic sensor may include a sensor circuit connected to at least one stretchable device according to example embodiments in FIGS. 1 to 15 of the present application.

The communication chipset in the mobile equipment device may be connected to an antenna. The communication chipset in the electronic patch may also be connected to an antenna. Using the antennas, the mobile equipment device and electronic patch may exchange power and data signals between each other.

The memory chip in the application processor of the mobile equipment device may be a non-volatile memory device such as flash memory, a phase-change random access memory (PRAM), a magneto-resistive RAM (MRAM), a resistive RAM (ReRAM), or a ferro-electric RAM (FRAM).

When the mobile equipment device is in communication proximity (e.g., adjacent) to the electronic patch, the electronic patch may receive a power and data signal from the mobile equipment device. The power and data signal may be received by the antenna of the electronic patch and transmitted to the communication chip of the electronic patch and supercapacitor. The power and data signal received by the electronic patch may be transmitted through the antenna of the electronic patch to the communication chip and supercapacitor. The supercapacitor may provide power to the optoelectronic sensor for operating the optoelectronic sensor.

When the optoelectronic sensor senses light, the optoelectronic sensor may transmit a signal to the communication chip of the electronic patch. The communication chip of the electronic patch may process signals received from the optoelectronic sensor and transmit the processed signals as power and data signals using the antenna of the electronic patch. The communication chip of the mobile equipment device may receive the power and data signals and transmit the received power and data signals to the controller. The controller may process the received power and data signals to the application processor, where the received signals may be analyzed using the CPU and stored in the memory chip.

The application processor may also control the communication chip of the mobile equipment device using the drive integrated circuit.

FIG. 55 is a circuit diagram of a sensor system according to example embodiments.

Referring to FIG. 55, in example embodiments, a circuit configured to process a signal generated from an optoelectronic device may including a sensing unit, a high pass filter (HPF), a low pass filter (LPF), and a gain amplifier. The sensing unit may include a light-emitting device LED and a photodiode (PD). The light-emitting device LED and/or photodiode PD may include one of the stretchable devices according to example embodiments in FIGS. 1-15 of the present application. One end of the LED may be connected to a first resistor R1 between the LED and a power supply pin Vcc. Another end of the LED may be connected to a node between a ground pin GND and a second resistor R2. One end of the photodiode PD be connected to a power-supply pin Vcc. The other end of the photodiode may be connected a node between a second resistor R2 and a line that connects to a first capacitor C1 in the high pass filter C1.

The high pass filter HPF may include the first capacitor C1, a second capacitor C2, an operation amplifier (hereinafter "HPF operational amplifier"), and resistors R3 to R6. The first and second capacitors C1 and C2 may be connected to a first terminal of the HPF operation amplifier. The first terminal may be (+) terminal. A ground pin GND may also be connected to a node between the second capacitor C2 and the first terminal through a third resistor R3. A node between the first and second capacitors C1 and C2 may be connected to a ground pin GND through the resistors R4 to R6 connected in series. A node between the fifth and sixth resistors R5 and R6 may be connected to a second terminal of the HPF operational amplifier. The second terminal may be a negative terminal (−).

As shown in FIG. 55, the low pass filter LPF may include resistors R7 to R10, capacitors C3 and C4 and an operational amplifier (hereinafter "LPF operational amplifier"). The output of the HPF operational amplifier may be connected to one end of the seventh resistor R7 in the low pass filter LPF. The resistors R7 and R8 may be connected in series to a first terminal of the LPF operational amplifier. The first terminal may be a positive (+) terminal. The third capacitor C3, ninth resistor 9, and tenth resistor 10 may be connected in series between a ground pin GND and a node between the seventh resistor R7 and the eighth resistor R8. A node between the ninth resistor R9 and the tenth resistor R10 may be connected to the second terminal of the LPF operational amplifier. The second terminal of the LPF operational amplifier may be a negative (−) terminal.

The gain amplifier may include an operational amplifier (hereinafter "gain operational amplifier") and resistors R11 and R12 connected in series from the output of the gain operational amplifier to a ground pin GND. The output of the LPF operational amplifier may be connected to a first terminal of the gain operational amplifier. The first terminal of the gain operational amplifier may be a positive terminal (+).

As described above, according to example embodiments, a stretchable/foldable optoelectronic device having excellent characteristics may be realized. The stretchable/foldable optoelectronic device may have excellent durability. Even when a wavy structure of an optoelectronic device portion is stretched, electrical and optical characteristics of the stretchable/foldable optoelectronic device may be stably maintained until the wavy structure becomes a planar structure. Also, when the optoelectronic device portion is located on or around an MNP, even when the stretchable/foldable optoelectronic device is greatly/repeatedly deformed, the optoelectronic device portion may suffer no or little stress. Also, since graphene has excellent flexibility and high mechanical strength, the graphene may maintain its own characteristics/functions even with a bending radius of 1 mm or less and may be freely stretched in the wavy structure. Also, QDs have high color purity, high quantum yield, high stability, and self light-emitting characteristics and are stretchable and foldable in the wavy structure, and colors of light are easily adjusted by changing the sizes of QDs. Since a QD-containing layer may be a light-emitting layer, the stretchable/foldable optoelectronic device may be a device having a stretchable or foldable light-emitting surface. The stretchable/foldable optoelectronic device may have tensile strain that is equal to or greater than about 5% or about 100% and may normally operate without any drop in brightness or luminous efficiency even with a bending radius of 1 mm or less.

The stretchable/foldable optoelectronic device according to example embodiments may be applied for various purposes to various devices such as a next-generation mobile display, a stretchable surface light-emitting apparatus, a transparent display that is used by being attached to a curved glass surface, a wearable display, a patch-type light source for bio-sensing, a PPG sensor, and a light source that is used in surgical gloves. The afore-described specific applications are non-limiting examples and the stretchable/foldable optoelectronic device may be applied to other various devices.

It should be understood that example embodiments described herein should be considered in a descriptive sense only and not for purposes of limitation. Descriptions of features or aspects within each device or method according to example embodiments should typically be considered as available for other similar features or aspects in other devices or methods according to example embodiments. For example, it will be understood by one of ordinary skill in the art that configurations of the stretchable/foldable optoelectronic devices of FIGS. 1 through 15 may be modified in various ways. For example, at least one selected from the group consisting of a graphene layer and a QD-containing layer may be replaced by another material and a stack structure of an optoelectronic device portion may be modified in various ways. Also, it will be understood that the methods of manufacturing the stretchable/foldable optoelectronic devices of FIGS. 17 through 24 may be modified in various ways. It will be understood that the principle/spirit applied to the stretchable/foldable optoelectronic device according to one or more embodiments may be applied to other devices. Accordingly, the scope of inventive concepts is not limited by the detailed description but by the technical spirit of the appended claims.

While some example embodiments have been particularly shown and described, it will be understood by one of ordinary skill in the art that variations in form and detail may be wade therein without departing from the spirit and scope of the claims.

What is claimed is:

1. A stretchable optoelectronic device comprising:
a substrate that includes an elastomeric polymer and is stretchable;
an optoelectronic device portion on the substrate, the optoelectronic device portion including a graphene layer and a quantum dot (QD)-containing layer, the optoelectronic device portion being configured to have a wavy structure to be stretchable; and
a plastic material layer connected to a surface of the optoelectronic device portion, wherein
the plastic material layer is between the substrate and the optoelectronic device portion or the optoelectronic device portion is between the substrate and the plastic material layer, and
the plastic material layer has a thickness that ranges from about 0.5 μm to about 30 μm.

2. The stretchable optoelectronic device of claim 1, further comprising:
a capping layer including an elastomeric polymer, wherein
the capping layer is stretchable, and
the capping layer is on the optoelectronic device portion.

3. The stretchable optoelectronic device of claim 2, wherein the optoelectronic device portion is located on a mechanical neutral plane (MNP) or around a MNP.

4. The stretchable optoelectronic device of claim 2, wherein
the elastomeric polymer of the capping layer includes at least one of polyurethane (PU), polyurethane acrylate (PUA), acrylate polymer, acrylate terpolymer, and silicon-based polymer.

5. The stretchable optoelectronic device of claim 4, wherein the silicon-based polymer includes at least one of polydimethylsiloxane (PDMS), polyphenyl-methylsiloxane, and hexamethyldisiloxane.

6. The stretchable optoelectronic device of claim 1, wherein the plastic material layer includes at least one of polyethylene naphthalate (PEN), polyimide (PI), and polyethylene terephthalate (PET).

7. The stretchable optoelectronic device of claim 1, wherein
the wavy structure of the optoelectronic device portion has an average wavelength that ranges from about 10 μm to about 2 mm, and
the wavy structure of the optoelectronic device portion has an average amplitude that ranges from about 100 nm to about 1 mm.

8. The stretchable optoelectronic device of claim 1, wherein the optoelectronic device portion is one of a light-emitting device portion, a photovoltaic device portion, and a photo-detecting device portion.

9. The stretchable optoelectronic device of claim 1, wherein
the optoelectronic device portion includes a first electrode on the substrate, a light-emitting layer on the first electrode, and a second electrode on the light-emitting layer,
one of the first and second electrodes is an anode,
the anode includes the graphene layer, and
the light-emitting layer includes the QD-containing layer.

10. The stretchable optoelectronic device of claim 9, wherein the optoelectronic device portion further includes at least one of:
a hole transport layer (HTL) between the anode and the light-emitting layer; and
an electron transport layer (ETL) between the light-emitting layer and a cathode from among the first and second electrodes.

11. The stretchable optoelectronic device of claim 10, wherein the optoelectronic device portion further includes a hole injection layer (HIL) between the anode and the HTL.

12. The stretchable optoelectronic device of claim 1, wherein the optoelectronic device portion further includes a poly(3,4-ethylenedioxythiophene) (PEDOT) layer that contacts the graphene layer.

13. The stretchable optoelectronic device of claim 1, wherein the graphene layer is doped with a p-type dopant.

14. The stretchable optoelectronic device of claim 1, wherein the elastomeric polymer of the substrate includes at least one of silicon-based polymer, polyurethane (PU), polyurethane acrylate (PUA), acrylate polymer, and acrylate terpolymer.

15. The stretchable optoelectronic device of claim 14, wherein the silicon-based polymer includes at least one of polydimethylsiloxane (PDMS), polyphenyl-methylsiloxane, and hexamethyldisiloxane.

16. The stretchable optoelectronic device of claim 1, wherein the stretchable optoelectronic device has strain that is equal to or greater than 5%.

17. The stretchable optoelectronic device of claim 1, wherein the stretchable optoelectronic device is a foldable device.

18. An apparatus comprising:
the stretchable optoelectronic device of claim 1; and
a circuit connected to the stretchable optoelectronic device.

19. A light-emitting device comprising:
a first material layer that includes an elastomeric polymer;
a second material layer that faces the first material layer and includes an elastomeric polymer; and
a light-emitting device portion between the first and second material layers, the light-emitting device portion including a light-emitting layer that includes a quantum dot (QD)-containing layer, the light-emitting device portion being configured so that a light-emitting surface of the light-emitting layer is one of stretchable and foldable, wherein
the light-emitting device portion includes a first electrode, a hole transport layer (HTL), the light-emitting layer, an electron transport layer (ETL), and a second electrode that are sequentially stacked on the first material layer or the second material layer, and
the first electrode includes graphene.

20. The light-emitting device of claim 19, wherein
the light-emitting device portion further includes a graphene layer,
the graphene layer is between the light-emitting layer and one of the first material layer and the second material layer.

21. The light-emitting device of claim 20, further comprising:
a plastic layer between the light-emitting device portion and one of the first material layer and the second material layer,
wherein the graphene layer is between the plastic layer and the QD-containing layer.

22. The light-emitting device of claim 21, wherein the plastic layer includes at least one of polyethylene naphthalate (PEN), polyimide (PI), and polyethylene terephthalate (PET).

23. The light-emitting device of claim 19, wherein the light-emitting device portion is configured to have a wavy structure.

24. The light-emitting device of claim 19, wherein the elastomeric polymer in at least one of the first material layer and the second material layer includes at least one of silicon-based polymer, polyurethane (PU), polyurethane acrylate (PUA), acrylate polymer, and acrylate terpolymer.

25. The light-emitting device of claim 24, wherein the silicon-based polymer includes at least one of polydimethylsiloxane (PDMS), polyphenyl-methylsiloxane, and hexamethyldisiloxane.

26. An apparatus comprising:
the light-emitting device of claim 19; and
a circuit connected to the light-emitting device.

27. A stretchable optoelectronic device comprising:
a substrate including an elastomeric polymer that is stretchable;
an optoelectronic device portion on the substrate,
the optoelectronic device portion including a graphene layer and an active layer,
the active layer being on the graphene layer or between the graphene layer and the substrate,
the active layer including one of quantum dots, light-emitting nanomaterials, and a transition metal dichalcogenide (TMDC),
the optoelectronic device portion being configured to have a wavy structure if the substrate is not subject to a tensile stress, and
the optoelectronic device portion being configured to transition from the wavy structure to a planar structure based on a level of the tensile stress applied to the substrate, wherein
the graphene layer is a first electrode of the optoelectronic device portion,
the optoelectronic device portion includes a second electrode connected to the active layer, and
the optoelectronic device portion includes at least one of,
a hole transfer layer between the graphene layer and the active layer, and
an electron transfer layer between the second electrode and the active layer.

28. The stretchable optoelectronic device of claim 27, wherein the elastomeric polymer of the substrate includes at least one of silicon-based polymer, polyurethane (PU), polyurethane acrylate (PUA), acrylate polymer, and acrylate terpolymer.

29. The stretchable optoelectronic device of claim 27, further comprising:
a capping layer on the optoelectronic device portion, wherein
the optoelectronic device portion is between the first substrate and the second substrate,
and
the capping layer includes at least one of silicon-based polymer, polyurethane (PU), polyurethane acrylate (PUA), acrylate polymer, and acrylate terpolymer.

30. The stretchable optoelectronic device of claim 27, wherein
the active layer includes the quantum dots, and
the quantum dots have one of a single-layer structure and a multi-layer structure.

31. The stretchable optoelectronic device of claim 27, wherein the active layer directly contacts at least one of the hole transfer layer and the electron transfer layer.

32. The stretchable optoelectronic device of claim 27, further comprising:
a plastic material layer, wherein
the plastic material layer includes at least one of polyethylene naphthalate (PEN), polyimide (PI), and polyethylene terephthalate (PET),
the plastic material layer is one of on the optoelectronic device portion and between the optoelectronic device portion and the substrate.

33. A sensor system, comprising:
an electronic patch including a stretchable optoelectronic device connected to a communication chip and an antenna; and a mobile equipment device configured to exchange data and power signals with the electronic patch, wherein the stretchable optoelectronic device includes a substrate and an optoelectronic device portion on the substrate, the substrate includes an elastomeric polymer that is stretchable, the optoelectronic device portion includes a graphene layer and an active layer, the active layer is on the graphene layer or between the graphene layer and the substrate, the active layer includes one of quantum dots, light-emitting nanomaterials, and a transition metal dichalcogenide (TMDC), the optoelectronic device portion is configured to have a wavy structure if the substrate is not subject to a tensile stress, and the optoelectronic device portion is configured to transition from the wavy structure to a planar structure based on a level of the tensile stress applied to the substrate.

34. The sensor system of claim 33, wherein the communication chip and the antenna in the electronic patch are a first communication chip and a first antenna respectively, and the mobile equipment device includes an application processor, a drive integrated circuit, and a second communication chip connected a second antenna.

35. A sensor circuit comprising:

a sensing unit including a stretchable optoelectronic device;

a filter circuit connected to the sensing unit; and a gain amplification circuit connected to the filter circuit, wherein the stretchable optoelectronic device includes a substrate and an optoelectronic device portion on the substrate, the substrate includes an elastomeric polymer that is stretchable, the optoelectronic device portion includes a graphene layer and an active layer, the active layer is on the graphene layer or between the graphene layer and the substrate, the active layer includes one of quantum dots, light-emitting nanomaterials, and a transition metal dichalcogenide (TMDC), the optoelectronic device portion is configured to have a wavy structure if the substrate is not subject to a tensile stress, and the optoelectronic device portion is configured to transition from the wavy structure to a planar structure based on a level of the tensile stress applied to the substrate.

36. The sensor circuit of claim 35, wherein the filter circuit includes a high pass filter circuit connected to a low pass filter circuit, the high pass filter circuit includes two capacitors connected in series to a terminal of a first operational amplifier, and the low pass filter circuit includes two resistors connected in series between an output terminal of the first operational amplifier and an input terminal of a second operational amplifier.

37. The sensor circuit of claim 36, wherein the gain amplification circuit includes a gain operational amplifier connected to an output terminal of the second operational amplifier.

* * * * *